United States Patent [19]

Kitano et al.

[11] Patent Number: 5,514,711
[45] Date of Patent: May 7, 1996

[54] STYRENE DERIVATIVES

[75] Inventors: Yasunori Kitano, Yokohama; Hisao Takayanagi, Yamato; Koichi Sugawara, Yokohama; Hiroto Hara, Machida; Hideo Nakamura, Suginami; Toshiko Oshino, Kawasaki, all of Japan

[73] Assignee: Mitsubishi Chemical Corporation, Tokyo, Japan

[21] Appl. No.: 369,263

[22] Filed: Jan. 5, 1995

Related U.S. Application Data

[63] Continuation of Ser. No. 961,315, Oct. 15, 1992, abandoned.

[30] Foreign Application Priority Data

Oct. 15, 1991 [JP] Japan .................... 3-266461
Oct. 5, 1992 [JP] Japan .................... 4-266027

[51] Int. Cl.$^6$ .................... A61K 31/275; C07C 255/34
[52] U.S. Cl. .................... 514/521; 514/522; 558/401; 558/403
[58] Field of Search .................... 558/401, 403; 514/523, 521

[56] References Cited

U.S. PATENT DOCUMENTS

| | | | |
|---|---|---|---|
| 5,041,602 | 8/1991 | Nagai et al. | 558/401 |
| 5,057,538 | 10/1991 | Shiraishi et al. | 558/401 X |
| 5,063,243 | 11/1991 | Cho et al. | 558/401 X |
| 5,135,950 | 8/1992 | Pippuri et al. | 558/401 X |
| 5,196,147 | 3/1993 | Taketani et al. | 558/401 X |
| 5,446,194 | 8/1995 | Bäckström et al. | 558/401 |

FOREIGN PATENT DOCUMENTS

| | | |
|---|---|---|
| 0322738 | 5/1989 | European Pat. Off. . |
| 323631 | 7/1989 | European Pat. Off. . |
| 426468 | 5/1991 | European Pat. Off. . |
| 62/39523 | 2/1987 | Japan . |
| 62/39522 | 2/1987 | Japan . |
| 62/277347 | 12/1987 | Japan . |
| 63/150237 | 6/1988 | Japan . |
| 63/154663 | 6/1988 | Japan . |
| 63/222153 | 9/1988 | Japan . |
| 2/138238 | 5/1990 | Japan . |
| 2/196715 | 8/1990 | Japan . |
| 3/63213 | 3/1991 | Japan . |
| WO91/16892 | 11/1991 | WIPO . |

OTHER PUBLICATIONS

Gazit et al., J. Med. Chem. (1989) 32, pp. 2344–2352.
Gazit et al., J. Med. Chem., (1991) vol. 34, No. 6, pp. 1896–1907.
Shiraishi et al., Chem. Pharm. Bull., 36(3), pp. 974–981, (1988).
Bryckaert et al., Experimental Cell Research 199, pp. 255–261 (1992).
Anafi et al., The Journal of Biological Chemistry, vol. 267, No. 7, pp. 4518–4523, (Mar., 1992).
Selleri et al., Chemical Abstracts No. 106149v (1968).
Yoneda, et al.; Cancer Research, 51, pp. 4430–4435 (1991).
Reddy, et al.; Cancer Research, 52, pp. 36–36–3641 (1992).
Brunton, et al.; Cancer Chemother Pharmacol, 32, pp. 1–19 (1993).
Muñoz, et al.; FEBS Letters, 279, pp. 319–322 (1991).
Roifman, et al., Journal of Immunology, 146, pp. 2965–2971 (1991).
O'Rourke, et al., Nature, 358, pp. 253–255 (1992).
Salari, et al., FEBS Letters, 263, pp. 104–108 (1990).
Asahi, et al., FEBS Letters, 309, pp. 10–14 (1992).
Bilder, et al.; American Jour. of Physiology, 260, pp. C7–21, –C–7–30 (1991).
Merkel, et al.; Biochem. & Biophys. Res. Comm., 192, pp. 1319–1326 (1993).
Dhar. et al.; Amer. Soc. for Pharmacology, 37, pp. 519–525 (1990).
Schneider, et al., Int. Immunology, 4, pp. 447–558 (1992).

*Primary Examiner*—Joseph Paul Brust
*Attorney, Agent, or Firm*—Wenderoth, Lind & Ponack

[57] ABSTRACT

Styrene derivatives of the following general formula (I):

$$R^3-C=CR^1R^2 \quad (I)$$

with a phenyl ring bearing substituents $R^4$, $R^5$, $R^6$, $R^7$, $R^8$ or pharmaceutically acceptable salts thereof. A pharmaceutical composition useful as anticancer agent, which comprises the above compound as an essential component, is also provided.

6 Claims, No Drawings

STYRENE DERIVATIVES

This application is a continuation of now abandoned application, Ser. No. 07/961,315 filed Oct. 15, 1992, now abandoned.

The present invention relates to novel styrene derivatives. In more particular, it relates to styrene derivatives having an inhibitory activity on tyrosine-specific protein kinase (hereinafter referred to as "tyrosine kinase") and also inhibitory activity on cancer cell proliferation.

A lot of substances have been used for cancer chemotherapy, but in most cases they are not necessarily satisfactory, since they exhibit unsatisfactory pharmacological effect, and their inhibitory activity is not limited to cancer cells, which causes great side effects.

It is known that the receptor of proliferation factor controls differentiation and proliferation of cells and that a certain abnormal event causes abnormal proliferation and differentiation of cells which results in canceration. Above all, it has been evident that tyrosine kinase type receptors participate substantially in formation of cancer. It was found that these receptors show particular protein kinase activity specific to tyrosine and that this activity is great especially in cancer cells. On the basis of these findings, it has been proposed that the drugs which can inhibit specifically the tyrosine kinase activity of proliferation factor receptor would be anticancer agents having a novel mechanism and less side effects. Examples of such anticancer agents derived from microorganisms are Erbstatin, Lavendustin, Herbimycin A, Genistein and the like, and examples of synthesized agents are benzylidenemalonitrile derivatives (Japanese Patent Publication (not examined) No. 138238/1990, Journal of Medicinal Chemistry, 32, 2344 (1989); ibid. 34, 1896 (1991)), α-cyanocinnamide derivatives [Japanese Patent Publication (not examined) No. 222153/1988], 3, 5 -diisopropyl-4-hydroxystrene derivatives [Japanese Patent Publication (not examined) No. 39522/1987], 3, 5 -di-t-butyl-4-hydroxystyrene derivatives [Japanese Patent Publication (not examined) No. 39523/1987], Erbstatin analogs [Japanese Patent Publication (not examined) No. 277347/1987] and the like.

Known tyrosine kinase inhibitors all have insufficient inhibition and cannot be satisfactorily used as anticancer agents. It is an object of the present invention to provide novel anticancer agents which are easily available, which are specifically and highly active as tyrosine kinase inhibitors of proliferation factor receptor, and which have less side effects accordingly.

In view of the fact that there is an interaction between the phenolic hydroxy group and tyrosine kinase active site of said enzyme during the process of phosphorylation of tyrosine residue of protein and that there is a nucleophilic attack of the phenolic hydroxy group to adenosine triphosphate, the present inventors have presumed that introduction of a substituent, in particular electrophilic substitutent, near the phenol (or catechol) moiety of tyrosine derivatives would increase the acidity of phenol (catechol) moiety in comparison with original tyrosine derivatives and would simultaneously inhibit the nucleophilic attack, thereby enhancing inhibition of the enzyme activity. Based on such presumption, the inventors have made an extensive study, and found a series of particular compounds having potent enzyme inhibition as never seen before. The present invention is based on such finding. Thus, the present invention provides styrene derivatives of the following general formula (I):

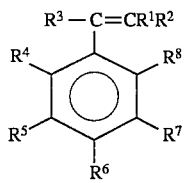

wherein, $R^1$ and $R^2$ independently each represent cyano group, $CONR^9R^{10}$ [wherein $R^9$ and $R^{10}$ independently each represent hydrogen atom, $C_1$–$C_5$ alkyl group or

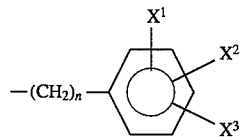

(in which n represents 0 or an integer of from 1 to 5, and $X^1$, $X^2$ and $X^3$ independently each represent hydrogen atom, halogen atom, $C_1$–$C_5$ alkyl group, $C_1$–$C_5$ alkoxy group, hydroxy group, nitro group or cyano group) with the proviso that $R^9$ and $R^{10}$ don't represent hydrogen atom at same time] or —$COR^{11}$ [wherein $R^{11}$ represents

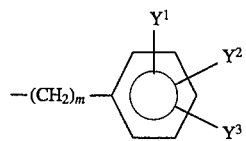

(in which m represents 0 or an integer of from 1 to 5, and $Y^1$, $Y^2$ and $Y^3$ independently each represent hydrogen atom, $C_1$–$C_5$ alkyl group, $C_1$–$C_5$ alkoxy group, hydroxy group, $C_1$–$C_5$ alkyl group or halogen atom)] but $R^1$ and $R^2$ don't represent cyano group at the same time;

$R^3$ represents hydrogen atom, $C_1$–$C_5$ alkyl group or hydroxy group, $R^4$, $R^5$, $R^6$, $R^7$ and $R^8$ independently each represent hydrogen atom, hydroxy group, halogen atom, $C_1$–$C_5$ alkoxy group, nitro group, cyano group;

—$NR^{12}R^{13}$ [wherein $R^{12}$ and $R^{13}$ independently each represent hydrogen atom, $C_1$–$C_5$ alkyl group or benzoyl group];

—$SO_pR^{14}$ [wherein p represents 0, 1 or 2, and $R^{14}$ represents $C_1$–$C_5$ alkyl group or phenyl group];

—$COR^{15}$ [wherein $R^{15}$ represents hydrogen atom, $C_1$–$C_5$ alkyl group, $C_1$–$C_5$ alkoxy group, hydroxy group, phenyl group, phenoxy group or —$NHR^{16}$ (in which $R^{16}$ represents $C_1$–$C_5$ alkyl group or phenyl group)] or $C_1$–$C_5$ alkyl group optionally substituted by halogen atom, with the proviso that at least one of $R^4$ to $R^8$ is hydroxy group, and that when $R^3$ is hydrogen atom and $R^4$ to $R^8$ independently each represent hydrogen atom, hydroxy group, $C_1$–$C_5$ alkoxy group, —$NR^{12}R^{13}$ (in which $R^{12}$ and $R^{13}$ are as defined above), $C_1$–$C_5$ alkyl group, then $R^1$ represents cyano group, $R^2$ represents —$CONR^9R^{10}$ [wherein $R^9$ represents hydrogen atom or $C_1$–$C_5$ alkyl group, $R^{10}$ represents

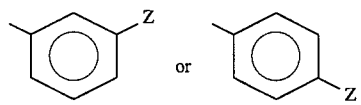

(in which Z represents $C_1$–$C_5$ alkyl group, halogen atom, nitro group or cyano group)

or —COR$^{11}$ [wherein R$^{11}$ represents

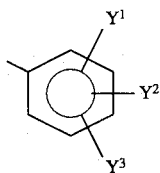

in which Y$^1$, Y$^2$ and Y$^3$ are as defined above), provided that R$^{11}$ is not

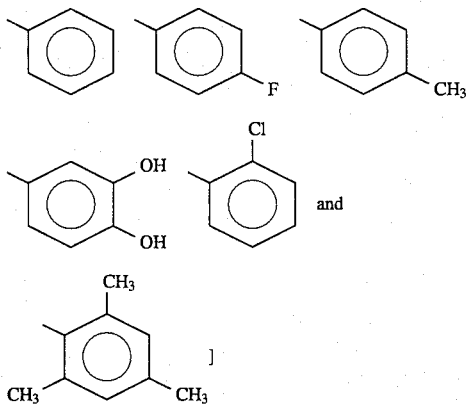

or pharmaceutically acceptable salts thereof.

The compounds of the present invention will be defined in more detail. Thus, the invention provides styrene derivatives of the following general formula (I)

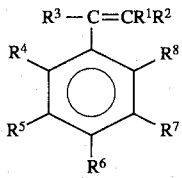     (I)

wherein, R$^1$ and R$^2$ represent cyano group, —CONR$^9$R$^{10}$ [wherein R$^9$ and R$^{10}$ independently each represent hydrogen atom, C$_1$–C$_5$ alkyl group (e.g. methyl group, propyl group, pentyl group, etc.) or

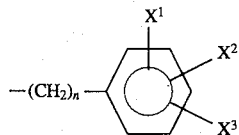

(in which n is 0 or an integer of from 1 to 5, X$^1$, X$^2$ and X$^3$ independently each represent hydrogen atom, halogen atom (e.g, fluorine atom, chlorine atom, bromine atom, iodine atom, etc.), C$_1$–C$_5$ alkyl group (e.g. methyl group, propyl group, pentyl group, etc.), C$_1$–C$_5$ alkoxy group (e.g. methoxy group, propoxy group, pentyloxy group, etc.), hydroxy group, nitro group or cyano group), with the proviso that R$^9$ and R$^{10}$ don't represent hydrogen atom at the same time] or —COR$^{11}$ [wherein R$^{11}$ represents

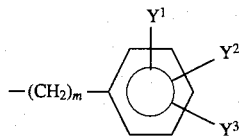

(in which m represents 0 or an integer of 1 to 5, and Y$^1$, Y$^2$ and Y$^3$ independently each represents hydrogen atom, C$_1$–C$_5$ alkoxy group (e.g. methoxy group, propoxy group, pentyloxy group, etc.), hydroxy group, C$_1$–C$_5$ alkyl group (methyl group, propyl group, pentyl group, etc.) or halogen atom (e.g. fluorine atom, chlorine atom, bromine atom, iodine atom. etc.)] with the proviso that R$^1$ and R$^2$ don't represent cyano group at the same time;

R$^3$ represents hydrogen atom, C$_1$–C$_5$ alkyl group (e.g. methyl group, propyl group, pentyl group, etc.) or hydroxy group;

R$^4$, R$^5$, R$^6$, R$^7$ and R$^8$ independently each represent hydrogen atom, hydroxy group, halogen atom (e.g. fluorine atom, chlorine atom, bromine atom, iodine atom, etc.), C$_1$–C$_5$ alkoxy group (e.g. methoxy group, propoxy group, pentyloxy group, etc.), nitro group, cyano group;

—NR$^{12}$R$^{13}$ [wherein R$^{12}$ and R$^{13}$ independently each represent hydrogen atom, C$_1$–C$_5$ alkyl group (e.g. methyl group, propyl group, pentyl group, etc.) or benzoyl group];

—SOpR$^{14}$ [wherein p represents 0, 1 or 2, and R$^{14}$ represents C$_1$–C$_5$ alkyl group (e.g. methyl group, propyl group, pentyl group, etc.) or phenyl group];

—COR$^{15}$ [wherein R$^{15}$ represents hydrogen atom, C$_1$–C$_5$ alkyl group (e.g. methyl group, propyl group, pentyl group, etc.), C$_1$–C$_5$ alkoxy group (e.g. methoxy group, propoxy group, pentyloxy group, etc.), hydroxy group, phenyl group, phenoxy group or —NHR$^{16}$ (in which R$^{16}$ represents C$_1$–C$_5$ alkyl group (e.g. methyl group, propyl group, pentyl group, etc.) or phenyl group)] or C$_1$–C$_5$ alkyl group (e.g. methyl group, propyl group, pentyl group, etc.) optionally substituted by halogen atom (e.g. fluorine atom, chlorine atom, bromine atom, iodine atom, etc.), with the proviso that at least one of R$^4$ to R$^8$ is hydroxy group, and that, when R$^3$ is hydrogen atom and R$^4$ to R$^8$ each represent hydrogen atom, hydroxy group, C$_1$–C$_5$ alkoxy group (e.g. methoxy group, propoxy group, pentyloxy group, etc.) —NR$^{12}$R$^{13}$ (in which R$^{12}$ and R$^{13}$ are as defined above) or unsubstituted C$_1$–C$_5$ alkyl group (e.g. methyl group, propyl group, pentyl group, etc), then R$^1$ represents cyano group, R$^2$ represents— CONR$^9$R$^{10}$ [wherein R$^9$ represents hydrogen atom or C$_1$–C$_5$ alkyl group (e.g. methyl group, propyl group, pentyl group, etc.), and R$^{10}$ represents

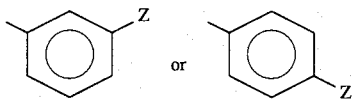

(in which Z represents C$_1$–C$_5$ alkyl group (e.g. methyl group, propyl group, pentyl group, etc.), halogen atom (e.g. fluorine atom, chlorine atom, bromine atom, iodine atom, etc.), nitro group or cyano group.)]

or —COR¹¹ [wherein R¹¹ represents

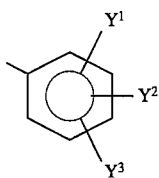

(in which Y¹, Y² and Y³ are as defined above), provided that R¹¹ is not

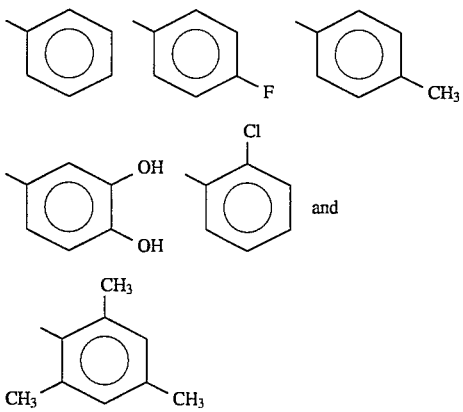

or pharmaceutically acceptable salts thereof.

Preferred are the compounds of the general formula (I) in which R¹ represents cyano group, R² represents —CONR⁹R¹⁰ [wherein R⁹ represents hydrogen atom or C₁–C₅ alkyl group, R¹⁰ represents

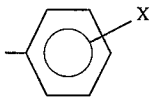

(in which X represents hydrogen atom, halogen atom, C₁–C₅ alkyl group, nitro group or cyano group)] or —COR¹¹ [wherein R¹¹ represents

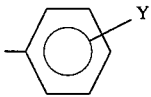

(in which Y represents hydrogen atom or halogen atom)], R³ represents hydrogen atom, C₁–C₅ alkyl group or hydroxy group, R⁴, R⁵, R⁶, R⁷ and R⁸ independently each represents hydrogen atom, hydroxy group, halogen atom, C₁–C₅ alkoxy group, nitro group, cyano group, —SO₂R¹⁴ (in which R¹⁴ represents C₁–C₅ alkyl group), carboxy group or C₁–C₅ alkyl group optionally substituted by halogen atom, provided that at least one of R⁴ to R⁸ is hydroxy group and that when R³ is hydrogen atom and R⁴ to R⁵ independently each represent hydrogen atom, hydroxy group, C₁–C₅ alkyl group or unsubstituted C₁–C₅ alkyl group, then R² represents —CONR⁹R¹⁰ [wherein R⁹ represents hydrogen atom and R¹⁰ represents

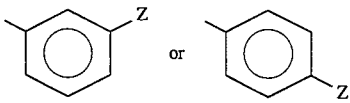

(in which Z represents C₁–C₅ alkyl group, halogen atom, nitro group or cyano group)] or —COR¹¹ [wherein R¹¹ represents

(in which Y represents halogen atom) provided that R¹¹ is not

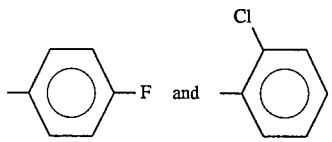

More preferable are the compounds of the general formula (I) above, in which R¹ represents cyano group, R² represents —CONR⁹R¹⁰ [wherein R⁹ represents hydrogen atom and R¹⁰ represents

(in which X represents hydrogen atom, halogen atom, C₁–C₅ alkyl group, nitro group or cyano group)] or —COR¹¹ [wherein R¹¹ represents

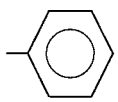

R³ represents hydrogen atom or hydroxy group, R⁴ and R⁸ independently each represent hydrogen atom, halogen atom, or nitro group, R⁵ and R⁷ independently each represent hydrogen atom, hydroxy group, halogen atom, C₁–C₅ alkoxy group, nitro group, cyano group, SO₂R¹⁴ (in which R¹⁴ represents C₁–C₅ alkyl group), carboxy group or C₁–C₅ alkyl group optionally substituted by halogen atom and R⁶ represents hydroxy group with the proviso that when R³, R⁴ and R⁸ are hydrogen atom and R⁵ and R⁷ independently each hydroxy group, C₁–C₅ alkoxy group or C₁–C₅ alkyl group, then R² represents —CONR⁹R¹⁰ [wherein R⁹ represents hydrogen atom and R¹⁰ represents

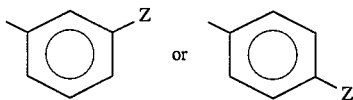

(in which Z represents C₁–C₅ alkyl group, halogen atom, nitro group or cyano group)].

Particularly preferable are the compounds of the general formula (I) in which R¹ represents cyano group, R² represents —CONR⁹R¹⁰ [wherein R⁹ represents hydrogen atom and R¹⁰ represents

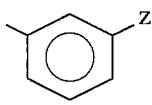

(in which Z represents hydrogen atom or halogen atom)], R³ represents hydrogen atom or hydroxy group, R⁴ represents hydrogen atom, R⁵ represents hydroxy group, halogen atom, C₁–C₅ alkoxy group or C₁–C₅ alkyl group, R⁶ represents hydroxy group, R⁷ represents hydrogen atom, halogen atom, cyano group or $C_1$–$C_5$ alkyl group and $R^8$ represents hydrogen atom, halogen atom or nitro group with the proviso that when $R^3$ and $R^8$ represent hydrogen atom, $R^5$ represents hydroxy group, $C_1$–$C_5$ alkoxy group or $C_1$–$C_5$ alkyl group, and $R^7$ represents hydrogen atom or $C_1$–$C_5$ alkyl group, then Z represents halogen atom.

Table 1 exemplifies practical embodiments of the compounds of the present invention.

TABLE 1

$$R^3-C=CR^1R^2$$ (attached to phenyl ring with $R^4, R^5, R^6, R^7, R^8$) (I)

| Compd. No. | $R^1$ | $R^2$ | $R^3$ | $R^4$ | $R^5$ | $R^6$ | $R^7$ | $R^8$ |
|---|---|---|---|---|---|---|---|---|
| 1 | —CN | —CONHPh | —H | —H | —OMe | —OH | —Cl | —H |
| 2 | —CN | —CONHPh | —H | —H | —OH | —OH | —Cl | —H |
| 3 | —CN | —CONH—C6H4—Cl | —H | —H | —OMe | —OH | —Cl | —H |
| 4 | —CN | —CONH—C6H4—Cl | —H | —H | —OH | —OH | —Cl | —H |
| 5 | —CN | —CONH—C6H4—Cl | —H | —H | —OMe | —OH | —Br | —H |
| 6 | —CN | —CONH—C6H4—Cl | —H | —H | —OH | —OH | —Br | —H |
| 7 | —CN | —CONH—C6H4—Cl | —H | —H | —OMe | —OH | —F | —H |
| 8 | —CN | —CONH—C6H4—Cl | —H | —H | —OH | —OH | —F | —H |

TABLE 1-continued $$R^3-C=CR^1R^2$$ with phenyl ring bearing $R^3, R^4, R^5, R^6, R^7, R^8$ (I)

| Compd. No. | $R^1$ | $R^2$ | $R^3$ | $R^4$ | $R^5$ | $R^6$ | $R^7$ | $R^8$ |
|---|---|---|---|---|---|---|---|---|
| 9 | —CN | —CONH—(4-Cl-phenyl) | —H | —H | —OH | —OH | —Br | —Br |
| 10 | —CN | —CONH—(4-Br-phenyl) | —H | —H | —OH | —OH | —H | —H |
| 11 | —CN | —CONH—(4-Br-phenyl) | —H | —H | —OH | —OH | —H | —H |
| 12 | —CN | —CONH—(4-Cl-phenyl) | —H | —H | —OH | —OH | —H | —H |
| 13 | —CN | —CONH—(4-Cl-phenyl) | —H | —H | —OH | —OH | —H | —H |
| 14 | —CN | —CONH—(4-Me-phenyl) | —H | —H | —OH | —OH | —H | —H |
| 15 | —CN | —CONH—(4-Cl-phenyl) | —H | —H | —OH | —OH | —CN | —H |

TABLE 1-continued $$R^3 \underset{R^4}{\overset{R^8}{-}} C=CR^1R^2 \quad (I)$$

with phenyl ring bearing R⁴, R⁵, R⁶, R⁷, R⁸

| Compd. No. | R¹ | R² | R³ | R⁴ | R⁵ | R⁶ | R⁷ | R⁸ |
|---|---|---|---|---|---|---|---|---|
| 16 | —CN | —CONH—C₆H₄—Cl | —H | —H | —OH | —OH | —H | —NO₂ |
| 17 | —CN | —CONH—C₆H₄—Cl | —H | —H | —OMe | —OH | —SO₂Me | —H |
| 18 | —CN | —COPh | —H | —H | —OH | —OH | —Br | —Br |
| 19 | —CN | —CONHPh | —H | —H | —OH | —OH | —I | —H |
| 20 | —CN | —CONH—C₆H₄—Cl | —H | —F | —OH | —OH | —F | —H |
| 21 | —CN | —CONH—C₆H₄—Cl | —H | —Cl | —OH | —OH | —Cl | —H |
| 22 | —CN | —CONH—C₆H₄—Cl | —H | —Cl | —OH | —OH | —Cl | —Cl |
| 23 | —CN | —CONH—C₆H₄—Cl | —H | —H | —Me | —OH | —Me | —H |
| 24 | —CN | —CONH—C₆H₄—Cl | —H | -tBu | —OH | -tBu | —F | —H |

TABLE 1-continued $R^3-C=CR^1R^2$ with phenyl bearing $R^4, R^5, R^6, R^7, R^8$ (I)

| Compd. No. | $R^1$ | $R^2$ | $R^3$ | $R^4$ | $R^5$ | $R^6$ | $R^7$ | $R^8$ |
|---|---|---|---|---|---|---|---|---|
| 25 | —CN | —CONH—(4-Cl-phenyl) | —H | —OH | —OH | —H | —CF$_3$ | —H |
| 26 | —CN | —CONH—(4-Cl-phenyl) | —H | —H | —OH | —OH | —OH | —H |
| 27 | —CN | —CONH—(4-Cl-phenyl) | —H | —H | —OH | —OH | —OH | —Cl |
| 28 | —CN | —CONH—(4-Cl-phenyl) | —H | —H | —OH | —OH | —NHCOPh | —H |
| 29 | —CN | —CONH—(4-Cl-phenyl) | —H | —H | —OH | —OH | —SO$_2$Ph | —H |
| 30 | —CN | —CONH—CH$_2$-phenyl | —H | —H | —OH | —OH | —Cl | —H |
| 31 | —CN | —CONH—(CH$_2$)$_3$-phenyl | —H | —H | —OH | —OH | —Cl | —H |

TABLE 1-continued $R^3-C=CR^1R^2$ (I)

(phenyl ring with $R^4, R^5, R^6, R^7, R^8$ substituents)

| Compd. No. | $R^1$ | $R^2$ | $R^3$ | $R^4$ | $R^5$ | $R^6$ | $R^7$ | $R^8$ |
|---|---|---|---|---|---|---|---|---|
| 32 | —CN | —CONH—(C6H4)—NO2 | —H | —H | —OH | —OH | —Cl | —H |
| 33 | —CN | —CONH—(C6H4)—CN | —H | —H | —OH | —OH | —Cl | —H |
| 34 | —CN | —CON(Et)—(C6H5) | —H | —H | —OH | —OH | —Cl | —H |
| 35 | —CN | —CONH—CH2—(C6H4)—OMe | —H | —H | —OH | —OH | —Cl | —H |
| 36 | —CN | —CONHPr | —H | —H | —OH | —OH | —Cl | —H |
| 37 | —CN | —CONH—(C6H4)—OEt | —H | —H | —OH | —OH | —Cl | —H |
| 38 | —CN | —CONH—(C6H3)(Me)(Me) | —H | —H | —OH | —OH | —Cl | —H |

TABLE 1-continued $R^3-C=CR^1R^2$ with phenyl ring bearing $R^3, R^4, R^5, R^6, R^7, R^8$ (I)

| Compd. No. | $R^1$ | $R^2$ | $R^3$ | $R^4$ | $R^5$ | $R^6$ | $R^7$ | $R^8$ |
|---|---|---|---|---|---|---|---|---|
| 39 | —CN | —CONH—(3,5-dichlorophenyl) | —H | —H | —OH | —OH | —Cl | —H |
| 40 | —CN | —CONH—(4-methoxyphenyl) | —H | —H | —OH | —OH | —Br | —Br |
| 41 | —CN | —CONH—(3,4-dichlorophenyl) | —H | —H | —OH | —OH | —Cl | —H |
| 42 | —CN | —CONH—(4-nitrophenyl) | —H | —H | —OH | —OH | —H | —H |
| 43 | —CN | —CONH—(4-cyanophenyl) | —H | —H | —OH | —OH | —H | —H |
| 44 | —CN | —CONH—(4-chlorophenyl) | —H | —H | —OH | —OH | —COPh | —H |
| 45 | —CN | —CONH—(4-chlorophenyl) | —H | —H | —OH | —OH | —CO$_2$Me | —H |

TABLE 1-continued $$R^3-C=CR^1R^2$$ with phenyl bearing $R^4, R^5, R^6, R^7, R^8$ (I)

| Compd. No. | R¹ | R² | R³ | R⁴ | R⁵ | R⁶ | R⁷ | R⁸ |
|---|---|---|---|---|---|---|---|---|
| 46 | —CN | —CONH-(4-Cl-phenyl) | —H | —H | —OH | —OH | —CONHPh | —H |
| 47 | —CN | —CONH-(3-Cl-phenyl) | —H | —Cl | —OH | —OH | —CONHPh | —H |
| 48 | —CONHPh | —CONH-(3-Cl-phenyl) | —H | —H | —OH | —OH | —CONHPh | —H |
| 49 | —CONH-(3-Cl-phenyl) | —CN | —H | —H | —OH | —OH | —Cl | —H |
| 50 | —CONH-(3-Cl-phenyl) | —CN | —H | —H | —OH | —OH | —Cl | —H |
| 51 | —CONH-(3-Cl-phenyl) | —COPh | —H | —H | —OH | —OH | —Br | —Br |
| 52 | —COPh | —COPh | —H | —H | —OH | —OH | —Cl | —H |
| 53 | —CN | —COPh | —H | —H | —OH | —OH | —Cl | —H |

TABLE 1-continued
$R^3-C=CR^1R^2$ (I)
| Compd. No. | $R^1$ | $R^2$ | $R^3$ | $R^4$ | $R^5$ | $R^6$ | $R^7$ | $R^8$ |
|---|---|---|---|---|---|---|---|---|
| 54 | —CN |  —CO-⟨C₆H₄⟩-Cl | —H | —H | —OH | —OH | —Cl | —H |
| 55 | —CN | —CO-⟨C₆H₄⟩-Cl | —H | —H | —OH | —OH | —Br | —Br |
| 56 | —CN | —CO-⟨C₆H₄⟩-Et | —H | —H | —OH | —OH | —Br | —H |
| 57 | —CN | —CO-⟨C₆H₄⟩-OH | —H | —H | —OH | —OH | —Cl | —H |
| 58 | —CN | —CO-⟨C₆H₅⟩ | —H | —F | —OH | —OH | —F | —H |
| 59 | —CN | —CO-⟨C₆H₅⟩ | —H | —NO₂ | —OH | —OH | —Br | —H |
| 60 | —CN | —CO-⟨C₆H₅⟩ | —H | —H | —Me | —OH | —Me | —Cl |

TABLE 1-continued
| Compd. No. | $R^1$ | $R^2$ | $R^3$ | $R^4$ | $R^5$ | $R^6$ | $R^7$ | $R^8$ |
|---|---|---|---|---|---|---|---|---|
| 61 | —CN | —CO—C$_6$H$_3$(OEt)— | —H | —H | —OH | —OH | —Cl | —Cl |
| 62 | —CN | —CO—C$_6$H$_4$— | —Me | —H | —OH | —OH | —Cl | —Cl |
| 63 | —CN | —CO—C$_6$H$_4$— | —Bu | —H | —OH | —OH | —Cl | —Cl |
| 64 | —CN | —CO—C$_6$H$_4$— | —OH | —H | —OH | —OH | —Cl | —Cl |
| 65 | —CN | —CO—C$_6$H$_4$— | —Me | —OMe | —OH | —OH | —Cl | —Cl |
| 66 | —CN | —CO—C$_6$H$_4$— | —Me | —H | —tBu | —OH | —tBu | —Cl |
| 67 | —CN | —CO—CH$_2$—C$_6$H$_4$— | —H | —H | —OH | —OH | —Br | —H |

TABLE 1-continued $$R^3-C=CR^1R^2$$

(structure with phenyl ring bearing $R^4, R^5, R^6, R^7, R^8$)

(I)

| Compd. No. | $R^1$ | $R^2$ | $R^3$ | $R^4$ | $R^5$ | $R^6$ | $R^7$ | $R^8$ |
|---|---|---|---|---|---|---|---|---|
| 68 | —CN | —CO—CH₂—CH₂—(4-Cl-C₆H₄) | —H | —H | —OH | —OH | —Cl | —H |
| 69 | —CN | —CO—CH₂—CH₂—(3-OMe-C₆H₄) | —H | —H | —OH | —OH | —Cl | —H |
| 70 | —CN | —CONH—C₆H₅ | —OH | —H | —OH | —OH | —Cl | —H |
| 71 | —CN | —CONH—C₆H₅ | —OH | —H | —OH | —OH | —OH | —Cl |
| 72 | —CN | —CONH—C₆H₅ | —OH | —H | —OH | —OH | —CN | —H |
| 73 | —CN | —CONH—C₆H₅ | —OH | —H | —Me | —OH | —Me | —Cl |
| 74 | —CN | —CONH—C₆H₅ | —OH | —H | —OH | —OH | —H | —NO₂ |

TABLE 1-continued $$R^3-C=CR^1R^2$$ with phenyl bearing $R^4, R^5, R^6, R^7, R^8$ (I)

| Compd. No. | $R^1$ | $R^2$ | $R^3$ | $R^4$ | $R^5$ | $R^6$ | $R^7$ | $R^8$ |
|---|---|---|---|---|---|---|---|---|
| 75 | —CN | —CONH—(phenyl) | —OH | —H | —OH | —OH | —Cl | —H |
| 76 | —CN | —CONH—(phenyl) | —OH | —Cl | —OH | —OH | —Cl | —H |
| 77 | —CN | —CONH—(4-NO₂-phenyl) | —OH | —Cl | —OH | —OH | —Cl | —H |
| 78 | —CN | —CONH—(2-Cl-phenyl) | —OH | —H | —OH | —OH | —Cl | —H |
| 79 | —CN | —CONH—(phenyl) | —Me | —H | —OH | —OH | —Cl | —H |
| 80 | —CN | —CONH—(phenyl) | —Me | —F | —OH | —OH | —F | —H |
| 81 | —CN | —CONH—(phenyl) | —Me | —H | —OH | —OH | —F | —NO₂ |

TABLE 1-continued $$R^3-C=CR^1R^2 \text{ with phenyl bearing } R^4, R^5, R^6, R^7, R^8 \quad (I)$$

| Compd. No. | R¹ | R² | R³ | R⁴ | R⁵ | R⁶ | R⁷ | R⁸ |
|---|---|---|---|---|---|---|---|---|
| 82 | —CN | —CONH-phenyl | —Me | —H | —OH | —OH | —CN | —H |
| 83 | —CN | —CONH-(Cl-phenyl) | —Me | —H | —OMe | —OH | —SO₂Me | —H |
| 84 | —CN | —CONH-(Cl-phenyl) | —Me | —H | —OH | —OH | —Br | —Br |
| 85 | —CONH-phenyl | —CN | —Me | —H | —OH | —OH | —Cl | —H |
| 86 | —CN | —CONH-(Cl-phenyl) | —Bu | —H | —OH | —OH | —Cl | —H |
| 87 | —CN | —CONH-CH₂-phenyl | —Bu | —H | —OH | —OH | —Cl | —H |
| 88 | —CN | —CONH-CH₂-phenyl | —Bu | —H | —OH | —OH | —Cl | —NO₂ |

TABLE 1-continued $R^3-C=CR^1R^2$ (I)

(phenyl ring with R^4, R^5, R^6, R^7, R^8 substituents)

| Compd. No. | R¹ | R² | R³ | R⁴ | R⁵ | R⁶ | R⁷ | R⁸ |
|---|---|---|---|---|---|---|---|---|
| 89 | —CN | —CONH-phenyl | -iPr | —H | —OH | —OH | —Cl | —H |
| 90 | —CO-(4-Cl-phenyl) | —CO-(4-Cl-phenyl) | —H | —H | —OH | —OH | —Cl | —H |
| 91 | —CO-(4-Cl-phenyl) | —CO-(4-Cl-phenyl) | —Me | —H | —OH | —OMe | —Cl | —H |
| 92 | —CO-(4-Br-phenyl) | —CO-(4-Cl-phenyl) | —Me | —H | —OH | —OH | —F | —H |
| 93 | —CO-(4-Br-phenyl) | —CO-(4-Cl-phenyl) | —H | —H | —OH | —OH | —F | —H |
| 94 | —COPh | —CO-CH₂-phenyl | —H | —H | —OH | —OH | —F | —H |
| 95 | —CN | —CONH-(3-Cl-phenyl) | —H | —H | —OMe | —OH | —NO₂ | —H |

TABLE 1-continued $R^3-C=CR^1R^2$ with phenyl bearing $R^4, R^5, R^6, R^7, R^8$ (I)

| Compd. No. | $R^1$ | $R^2$ | $R^3$ | $R^4$ | $R^5$ | $R^6$ | $R^7$ | $R^8$ |
|---|---|---|---|---|---|---|---|---|
| 96 | —CN | —CONH—(4-Cl-phenyl) | —H | —H | —OH | —OH | —NO$_2$ | —H |
| 97 | —CN | —CONH—(4-Cl-phenyl) | —H | —H | —OMe | —OH | —CF$_3$ | —H |
| 98 | —CN | —CONH—(4-Cl-phenyl) | —H | —H | —OH | —OH | —CF$_3$ | —H |
| 99 | —CN | —CONHPh | —H | —F | —OH | —OH | —F | —H |
| 100 | —CN | —CONH—(4-Cl-phenyl) | —H | —H | —Br | —OH | —Br | —H |
| 101 | —CN | —CONH—(4-Cl-phenyl) | —H | —H | —OMe | —OH | —Me | —H |
| 102 | —CN | —CONH—(4-Cl-phenyl) | —H | —H | —CO$_2$H | —OH | —H | —H |
| 103 | —CN | —CONH—(4-Cl-phenyl) | —H | —H | —OMe | —OH | —H | —H |

TABLE 1-continued $$R^3-C=CR^1R^2$$ with phenyl ring bearing $R^4, R^5, R^6, R^7, R^8$ (I)

| Compd. No. | $R^1$ | $R^2$ | $R^3$ | $R^4$ | $R^5$ | $R^6$ | $R^7$ | $R^8$ |
|---|---|---|---|---|---|---|---|---|
| 104 | —CN | —CONH—(4-Cl-phenyl) | —H | —H | —H | —OH | —Cl | —H |
| 105 | —CN | —CONHPh | —H | —H | —OMe | —OH | —Br | —H |
| 106 | —CN | —CONHPh | —H | —H | —OMe | —OH | —F | —H |
| 107 | —CN | —CO—(4-Cl-phenyl) | —H | —H | —OH | —OH | —H | —H |
| 108 | —CN | —CO—(4-Cl-phenyl) | —H | —H | —OH | —OH | —H | —H |
| 109 | —CN | —CONH—(4-F-phenyl) | —H | —H | —OH | —OH | —H | —H |
| 110 | —CN | —CONH—(4-Cl-phenyl) | —H | —H | —OH | —OH | —Me | —H |
| 111 | —CN | —CONHPh | —H | —H | —OH | —OH | —F | —H |
| 112 | —CN | —CONHPh | —H | —H | —OH | —OH | —Br | —H |
| 113 | —CN | —CONH—CH₂Ph | —H | —H | —OH | —OH | —F | —H |

TABLE 1-continued $$R^3-C=CR^1R^2 \text{ with phenyl ring bearing } R^4, R^5, R^6, R^7, R^8$$

| Compd. No. | $R^1$ | $R^2$ | $R^3$ | $R^4$ | $R^5$ | $R^6$ | $R^7$ | $R^8$ |
|---|---|---|---|---|---|---|---|---|
| 114 | —CN | —CONH-(4-Cl-phenyl) | —H | —H | —O$^n$Bu | —OH | —F | —H |
| 115 | —CN | —CONHPh | —H | —H | —O$^n$Bu | —OH | —F | —H |
| 116 | —CN | —CONH-(4-Cl-phenyl) | —H | —H | —OiPr | —OH | —F | —H |
| 117 | —CN | —CONHPh | —H | —H | —OiPr | —OH | —F | —H |
| 118 | —CN | —CONH-(4-Cl-phenyl) | —H | —H | —O$^n$Bu | —OH | —H | —H |
| 119 | —CN | —CONH-phenyl | —OH | —H | —OH | —OH | —H | —H |
| 120 | —CN | —CONH-(4-Cl-phenyl) | —OH | —H | —OH | —OH | —H | —H |
| 121 | —CN | —CONH-(4-Me-phenyl) | —OH | —H | —OH | —OH | —H | —H |

TABLE 1-continued
| Compd. No. | R¹ | R² | R³ | R⁴ | R⁵ | R⁶ | R⁷ | R⁸ |
|---|---|---|---|---|---|---|---|---|
| 122 | —CN | —CON(Et)(Ph) | —Me | —H | —OH | —OH | —H | —H |

In Table 1, Me means methyl group, Et means ethyl group, Pr means propyl group, Bu means butyl group and Ph means phenyl group.

The compounds of the general formula (I) can be converted to their salts with a base. The bases may be those which can make a salt with the compound of the general formula (I) above. Illustrative examples of such salts are metallic salts such as sodium salt, magnesium salt, aluminum salt and the like, and amine salts such as ammonium salt, methylamine salt, ethylamine salt, diethylamine salt, triethylamine salt, pyrrolidine salt, piperidine salt, morpholine salt, pyridine salt, aniline salt, and the like.

The compounds of the general formula (I) above can be prepared, for example, through the following route:

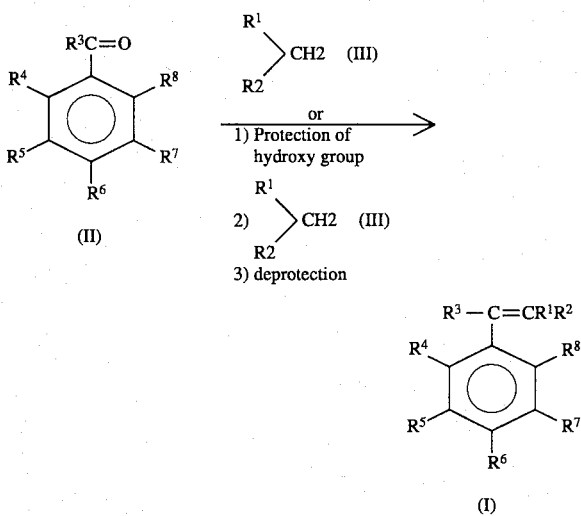

In the above formulae, $R^1$ to $R^8$ are as defined in the general formula (I) above, and $R^3$ represents hydrogen atom, chlorine atom, hydroxy group or $C_1$–$C_5$ alkyl group.

(1) Production of the compounds wherein $R^3$ is hydrogen atom or $C_1$–$C_5$ alkyl group: The compounds can be prepared by condensing the compound of the general formula (II) above (in which $R^{17}$ represents hydrogen atom or $C_1$–$C_5$ alkyl group) with the active methylene compound of the general formula (III) above with or without acid or base as a catalyst in appropriate solvent such as ethanol or benzene. Examples of the acids used as catalyst are protic acid such as sulfuric acid, and p-toluenesulfonic acid, and Lewis acid such as boron trifluoride, or the like. Examples of the bases usable as catalyst are ammonia or its salts; organic bases such as piperidine, pyridine, morpholine, 1, 8-diazabicyclo [5, 4, 0] undeca-7-ene or salts thereof; alkyl metal hydroxides such as sodium hydroxide, potassium hydroxide or the like; alkali metal amide such as lithium diisopropylamide or the like; metal alkoxide such as sodium methoxide or the like; alkali metal hydride such as sodium hydride, potassium hydride or the like.

The compounds of the general formula (I) wherein $R^1$ is cyano group and $R^2$ is —$CONHR^9R^{10}$ (in which $R^9$ and $R^{10}$ are as defined above) can be also prepared, for example, by condensing the compound of the general formula (II) above with cyanoacetic acid to give the compound of the following general formula (IV):

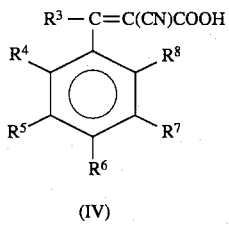

(in which $R^3$ to $R^8$ are as defined in the general formula (I) above) and then reacting said compound (IV) with the amine of the following general formula (V):

$$R^9R^{10}NH \qquad (V)$$

(in which $R^9$ and $R^{10}$ are as defined in the general formula (I) above) in an appropriate solvent such as tetrahydrofuran, benzene, dimethylformamide or the like or without solvent in the presence or absence of a condensing agent. Said acids and bases are usable as a condensing agent, and moreover inorganic condensing agents such as phosphoryl oxychloride, thionyl chloride or the like, and organic condensing agents such as dicyclohexylcarbodiimide, carbonyl diimidazole or the like can be used.

(2) Production of the compounds of wherein $R^3$ is hydroxy group:

Of the compounds of the general formula (II) above, for example, the compound in which $R^3$ is hydroxy group is subjected to reaction with trialkylsilane chloride such as trimethylsilane chloride, dimethyl-t-butylsilane chloride or the like or organic acid anhydride such as acetic anhydride, propionic anhydride or the like in the presence of nitrogen-containing compound such as triethylamine, pyridine, imidazole or the like in a hydrocarbon solvent such as benzene, toluene or the like or in a halogen type solvent (e.g. methylene chloride) or in an aprotic solvent (e.g. dimethylformamide) or to reaction with an organic acid anhydride such as acetic anhydride, propionic anhydride or the like which also functed as a solvent in the presence of a catalytic amount of mineral acid such as sulfuric acid, hydrochloric acid or the like, protonic acid such as p-toluenesulfonic acid or the like or Lewis acid such as boron trifluoride or the like, whereby said compound (II) in which at least one of $R^4$ to $R^8$ is acyloxy group or trialkylsiloxy group can be obtained. This product is allowed to react with thionyl chloride or oxalyl chloride in hydrocarbon solvent such as benzene, toluene or the like or halogen type solvent such as methylene chloride or the like to give the compound of the general formula (II) above in which $R^3$ is chlorine atom and at least one of $R^4$ to $R^8$ is acyloxy group or trialkylsiloxy group. This compound is allowed to react with the compound of the general formula (III) above or its alkali metal salt in hydrocarbon solvent such as benzene, toluene or the like or halogen type solvent such as methylene chloride or the like in the presence or absence of a base such as triethylamine, pyridine or the like to give the compound of the general formula (I) above. When the acyloxy group or trialkylsiloxy group remains in the product, these groups can be hydrolyzed if necessary. For example, acyloxy group may be hydrolyzed with alkali metal hydroxide such as sodium hydroxide or the like in a solvent such as water, methanol, tetrahydrofuran or their mixture, and trialkylsiloxy group may be hydrolyzed with an acid, fluorine ion or the like in methanol, tetrahydrofuran or their mixture.

In particular, the compound of the general formula (I) in which $R^3$ is OH and either of $R^1$ and $R^2$ is —$CONR^9R^{10}$ (wherein $R^9$ and $R^{10}$ are as defined in the general formula (I)

above) can be prepared through the following route.

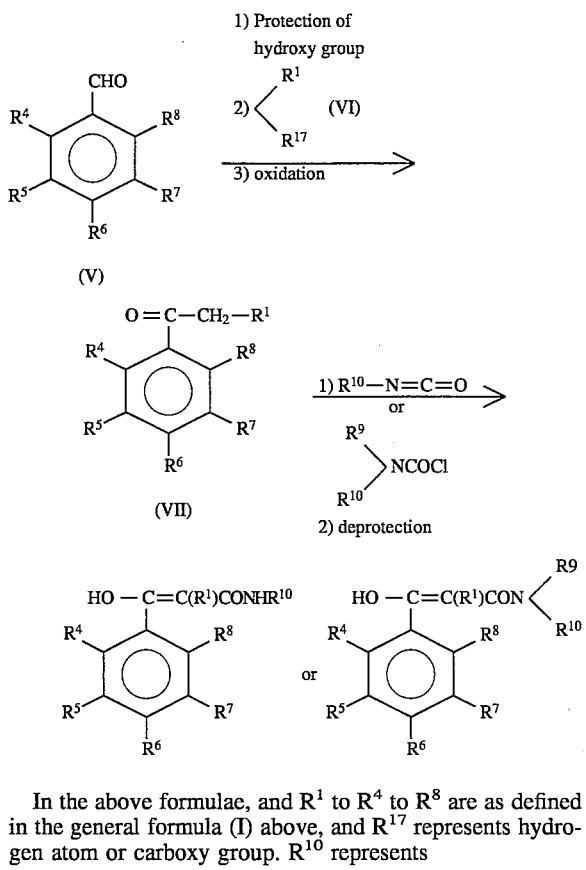

In the above formulae, and $R^1$ to $R^4$ to $R^8$ are as defined in the general formula (I) above, and $R^{17}$ represents hydrogen atom or carboxy group. $R^{10}$ represents

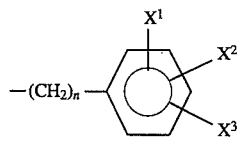

(in which $x^1$ to $x^3$ are as defined in the above general formula) and $R^9$ represents $C_1$–$C_5$ alkyl group.

The compound of the general formula (V) is properly treated for protecting the hydroxy group if necessary, allowed to react with the compound of the general formula (VI) in the presence of a base in a solvent such as diethyl ether, tetrahydrofuran or the like to give its adduct, and the latter is subjected to oxidation to give the compound of the general formula (VII). As bases, there are exemplified alkali metal amide such as lithium diisopropylamide or the like, organic metal compound such as butyllithium or the like, metal hydride such as sodium hydride or the like, and metal alcoholate such as sodium methylate or the like. Examples of the oxidizing agent are metallic oxidizing agent such as chromic acid, permanganic acid or the like, and organic oxidizing agent such as dimethyl sulfoxideoxalyl chloride or the like. Preferable protecting groups are those which can endure the reaction conditions, and include silyl group such as t-butyldimethylsilyl group or the like, substituted methyl group such as methoxymethyl group or the like, and benzyl group or the like.

The compounds of the general formula (I) or the salts thereof are useful as tyrosine kinase inhibitors as described below, and on the basis of such an activity, utility such as anticancer agents, immunosuppressive agents, platelet aggregation inhibitors, antiarteriosclerosis agents, antiinflammatory agents or the like can be expected therefrom.

Pharmaceutical formulation for the tyrosine kinase inhibitors and anticancer agents may be made in the manner suited for oral, enteral or parenteral administration. Examples of the formulation are tablets, capsules, granules, syrups, suppositories, ointments, in jections and the like.

Carriers for the pharmaceutical formulation as tryrosine kinase inhibitors and anticancer agents may be organic or inorganic, solid or liquid, ordinarily inert pharmaceutical carrier suited for oral, enteral or parenteral administration. Examples of such carriers are crystalline cellulose, gelatin, lactose, starch, magnesium stearate, talc, vegetable or animal type fats and oils, gum, polyalkylene glycol, etc. Ratio of the tyrosine kinase inhibitor, or anticancer agent of the present invention to the carrier in the formulation may be changed from 0.2% to 100%.

Formulations of the tyrosine kinase inhibitor or anticancer agent of the present invention may include other tyrosine kinase inhibitor, anticancer agent and other medicines miscible therewith. The tyrosine kinase inhibitor or anticancer agent of the present invention is not necessarily the main ingredient in such formulation.

The tyrosine kinase inhibitor or anticancer agent of the present invention may be administered in a dosage which can attain generally the desired effect without side effect. Such a dosage should be decided by practitioner's judgement, but in general, daily dosage for adult is 10 mg to 10 g, preferably 20 mg to 5 g. Daily dosage of the compound of the present invention for adult may be 1 mg to 5 g, preferably 3 mg to 1 g.

In order to evaluate tyrosine kinase inhibition and cancer cell proliferation inhibition of the compounds of the present invention, assay was effected on the partially purified human EGF (epidermal cell growth factor) receptor tyrosine kinase activity assaying system and cell culture system using human cancer cells. Further, of known inhibitors disclosed in patents and literatures, comparatively potent compounds were assayed simultaneously for comparing the inhibitory activity.

Test on Tyrosine Kinase Activity

Tyrosine kinase activity inhibition was assayed by improving the tyrosine kinase activity assaying method as described in Linda J. Pike at al., Proceedings of the National Academy of Sciences of the U.S.A. 79, 1443 (1982), using EGF receptor partially purified from A431 cell line derived from human squamous cell carcinoma.

Detailed explanation of the assaying method will be given below.

A431 cells were cultivated in Dulbecco's modified Eagle's medium (DMEM) containing 10% fetal calf serum (FCS) at 37° C. in a stream of 5% carbon dioxide, and the resultant cells were homogenized in a solution containing 10 mM N-2 -hydroxyethylpiperazino-N'-2-ethanesulfonic acid (Hepes) buffer (pH 7.4), 0.25M sucrose and 0.1 mM EDTA and centrifuged at 1000 g for 5 minutes. The supernatant was centrifuged at 27500×g for 30 minutes to give A431 cell membrane fraction, which was provided for the assay as the partially purified EGF receptor, enzyme source.

To a mixture of said A431 cell membrane fraction (10 to 15 µg), 15 mM Hepes buffer (pH 7.7), 2 mM $MnCl_2$, 10 µM $ZnSO_4$ and a test material (1% final concentration, DMSO) dissolved in dimethyl sulfoxide (DMSO) was added 100 ng EGF, and the resultant mixture was subjected to preincubation in ice for 10 minutes, and the reaction was initiated by adding 75 µg synthetic substrate RR-SRC peptide (Arg-Arg-Leu-Ile-Glu-Asp-Ala-Glu-Tyr-Ala-Ala-Arg-Gly) and 10 µMγ-$^{32}$ P-adenosine triphosphate (55.5 kBq/assay). At that time the volume was 60 µl. The reaction was allowed to proceed in ice for 30 minutes and stopped by adding 10 mg/ml bovine serum albumin (6 μl) and 20% trichloroacetic acid (25 μl). The mixture was allowed to stand in ice for 30 minutes.

Then the mixture was centrifuged at 5000×g for 2 minutes, and the supernatant (40 μl) was sampled and adsorbed on P81 phosphocellulose paper. The paper was fixed by dipping in 30% aqueous acetic acid for 15 minutes, washed by dipping in 15% aqueous acetic acid for 15 minutes (the washing was repeated 4 times), dipped in acetone for 5 minutes, dried, and the count of $^{32}P$ attached on P81 phosphocellulose paper was assayed with a liquid scintillation counter. The count obtained was defined as "A". At the same time, counts of the reaction not containing the test material and the reaction not containing both the test material and EGF were assayed, and the resulted counts were defined as "B" and "C" respectively.

Tyrosine kinase inhibitory rate was obtained according to the following equation:

Inhibitory Rate (%)=(B-A/B—C)×100 Further, $IC_{50}$ value (50% Inhibitory Concentration) was calculated from the inhibitory rate obtained by changing the concentration of the test material.

Test on Cancer Cells in Tissue Culture

SKOV3 cell line, which is from human ovary cancer, possesses excessive c-erbB2 onco-genes on the surface of the cell.

c-erbB2 gene product is a proliferation factor receptor type membrane protein having homology with EGF receptor and it shows tyrosine kinase activity as EGF receptor. Effect of the test material against the proliferation of cultivated cancer cells was examined with this SKOV3 cell line as follows:

SKOV3 cell was inoculated at a rate of $1×10^3$ cell/well on a 96 well dish, and cultivated on a DMEM: F12 (1:1) medium containing 10% FCS and 0.1 mg/ml kanamycin at 37° C. in a stream of 5% carbon dioxide for one day. Test material dissolved in DMSO was added to the medium (final concentration of DMSO was below 0.1%), which was cultivated for 3 days under the conditions mentioned above. Test material was replaced every 24 hours together with the medium.

Counting the number of living cells was effected by making colorimetric analysis at two wave lengths, 550 nm and 610 nm, in reference to the assaying method as described in Michael C. Alley et al., Cancer Research, 48, 589 (1988 using MTT reagent, and the number obtained was defined as "a".

At the same time, the count of the number of living cells obtained without adding the test material was assayed, and the number obtained was defined as "b".

Cell proliferation inhibitory rate was determined according to the following equation:

Inhibitory Rate (%)=(b–a)/b×100

The results are shown in Tables 2–5. Compound No. in the table corresponds to Compound No. in Table 1.

TABLE 2

Tyrosine Kinase Activity Inhibitory Effect

| Compound No. | Inhibitory Rate (%) in the presence of 10 μM | Reference* |
|---|---|---|
| HO-C6H3(OH)-CH=C(CN)-CONH-C6H5 | 41 | 1) |
| 10 | 47 | — |
| 11 | 77 | — |
| 12 | 52 | — |
| 13 | 100 | — |
| 14 | 77 | — |
| 1 | 63 | — |
| 2 | 74 | — |

TABLE 3

| Compound No. | $IC_{50}$ (μM) | Reference* |
|---|---|---|
| EtO-C6H2(OH)(CH2SPh)-CH=C(CN)-CONH2 | 2.6 | 2) |
| HO-C6H3(OH)-CH=CH-NHCHO | 12 | 3) |
| HO-C6H3(OH)-CH=C(CN)-C(=S)NH2 | 11 | 4) |
| 1 | 1.6 | — |
| 2 | 1.2 | — |
| 3 | 0.68 | — |
| 4 | 0.68 | — |
| 5 | 1.4 | — |
| 6 | 0.49 | — |
| 7 | 1.6 | — |
| 8 | 0.60 | — |
| 9 | 0.28 | — |
| 13 | 1.4 | — |
| 14 | 2.1 | — |
| 15 | 1.0 | — |
| 16 | 0.28 | — |
| 17 | 1.4 | — |
| 23 | 0.9 | — |
| 95 | 1.8 | — |
| 98 | 2.3 | — |
| 100 | 1.1 | — |
| 101 | 0.42 | — |
| 103 | 2.1 | — |

TABLE 3-continued

| Compound No. | IC$_{50}$ (μM) | Reference* |
| --- | --- | --- |
| 105 | 1.8 | — |
| 110 | 1.3 | — |
| 119 | 0.96 | — |

TABLE 4

| Compound No. | Inhibitory Rate (%) in the presence of 1 μM |
| --- | --- |
| 13 | 46 |
| 7 | 41 |
| 8 | 78 |

TABLE 5

Proliferation Inhibitory Effect Against Cultivated Cells

| Compound No. | IC$_{50}$ (μM) | Reference* |
| --- | --- | --- |
| HO-C6H3(OH)-CH=C(CN)-CONH-C6H5 | 35 | 1) |
| EtO-C6H2(OH)(CH2SPh)-CH=C(CN)-CONH2 | 78 | 2) |
| 1 | 17.3 | — |
| 2 | 20.4 | — |
| 4 | 21.6 | — |
| 6 | 21 | — |
| 8 | 23.4 | — |
| 9 | 17 | — |
| 13 | 30 | — |
| 15 | 34 | — |
| 16 | 24 | — |
| 98 | 16 | — |
| 100 | 19 | — |
| 105 | 13 | — |
| 110 | 14 | — |
| 119 | 24 | — |

Reference
1) A. Gazit, N. Osheroy, I. Posner, P. Yaish, E. Pradosu, C. Gilon, and A. Levitzki; J. Med. Chem., 34, 1896 (1991).
2) T. Shiraishi, K. Kameyama, N. Imai, T. Domoto, I. Kasumi, and K. Watanabe; Chem. P harm. Bull., 36, (1988).
3) H. Umezawa, M. Imoto, T. Sawa, K. Isshiki, N. Matsuda, T. Uchida, H. Iinuma, M. Hamada, T. Takeuchi, J. Antibiot. 39, 170 (1986).
4) A. Gazit, P. Yaish, C. Gilon, A. Levitzki, J. Med. Chem. 32, 2344 (1989).

It was evident from the results of Tables 2–5 that the compounds of the present invention show particularly excellent enzyme inhibitory activity and cell proliferation inhibitory activity in comparison with the tyrosine kinase inhibitors already known.

Toxicity Test

Toxicity test for the compounds of the present invention was examined in the manner as shown below.
Test compound: Compound No. 4
Test animal: Mouse ddy (male) 16–20 g
Dosage and Method of Measurement:

Test compound was suspended in a mixture of 0.25% carboxymethyl cellulose, physiological saline, and a small amount of Tween 80 to give a test solution. This solution was administered intraperitoneally at a dose of 0 mg/kg (control), 500 mg/kg and 1000 mg/kg to the test animal. Change of the body weight was measured 3 days later.

Test results:
No death was observed in both dosages of 500 mg/kg and 1000 mg/kg. Change of the body weight was as follows:

| Dosage | Change of the body weight |
| --- | --- |
| 500 mg/kg | +5.6 g |
| 1000 mg/kg | +6.1 g |
| Control (0 mg/kg) | +6.2 g |

Any substantial difference on the change of the body weight was not observed among the groups, and it was concluded that the compound of the present invention would show very low toxicity.

Presently preferred and practical embodiments of the present invention will be illustratively shown in the following examples.

EXAMPLE 1

Production of 2-cyano-3-(3-chloro-4-hydroxy-5-methoxyphenyl) propeneanilide (Compound No. 1 in Table 1):

To a solution of 5-chlorovanillin (728 mg, 3.9 mmol) and cyanoacetanilide (625 mg, 3.9 mmol) in ethanol (20 ml) were added 3 drops of piperidine, and the resulting mixture was refluxed for 2 hours. After cooling to room temperature, the resulting solid was filtered and washed with ethanol: water (1: 1) to give the objective 2-cyano- 3-(3-chloro-4-hydroxy-5-methoxyphenyl) propenanilide (950 mg, 74% in yield).

mp. 273° C.

$^1$HNMR (DMSO-d$_6$, 250 MHz) δ ppm: 3.89 (s, 3H), 7.12 (t, J=7.5 Hz, 1H), 7.36 (t, J = 7.5 Hz, 2H), 7.60–7.75 (m, 4H) 8.14 (s, 1H), 10.28 (s, 1H), 10.74 (brs, 1H)

EXAMPLE 2

Production of 2-cyano-3-(3-chloro-4, 5-dihydroxyphenyl)propenanilide (Compound No. 2 in Table 1):

To a solution of 2-cyano-3-(3-chloro-4-hydroxy-5-methoxyphenyl) propenanilide (340 mg, 1.03 mmol) in methylene chloride (20 ml) chilled at −70° C. was dropwise added 1M solution of boron tribromide in methylene chloride (2.50 ml, 2.5 mmol). The reaction mixture was gradually allowed to warm to room temperature and poured into water. The product was extracted with ethyl acetate, dried over MgSO$_4$ and concentrated. The resulting solid was suspended in diethyl ether, refluxed for 10 minutes and the resultant solid was filtered to give the objective 2-cyano- 3-(3-chloro-4, 5-dihydroxyphenyl) propenanilide (260 mg, 80% in yield).

mp, 227°–234° C.

$^1$HNMR (DMSO-d$_6$, 250 MHz) δ ppm: 7.12 (t, J=7.8 Hz, 1H), 7.35 (t, J = 7.8 Hz, 2H), 7.50 (d, J=1.9 Hz, 1H), 7.57 (t, J=1.9 Hz, 1H), 7.65 (d, J=7.8 Hz, 2H), 8.04 (s, 1H), 10.25 (s, 1H), 10.43 (brs, 1H), 10.54 (brs, 1H).

EXAMPLE 3

Production of N-(3-chlorophenyl)-2-cyano-3-(3-chloro-4-hydroxy-5-methoxyphenyl) propenamide (Compound No. 3 in Table 1):

In the same manner as in Example 1 were condensed 5-chlorovanillin (1.23 g, 6.59 mmol) and N-(3-chlorophenyl) cyanoacetamine (1.28 g, 6.59 mmol) suspended in diethyl ether (40 ml), refluxed for 10 minutes, allowed to cool to room temperature and filtered to give N-(3-chlorophenyl)-2-cyano-3-(3-chloro-4-hydroxy-5-methoxyphenyl) propenamide (1.30 g, 54% in yield).

mp. 225°–226 °C.

$^1$HNMR (DMSO-$d_6$, 250 MHz) δ ppm: 4.77 (s, 3H), 8.07 (d, J=8.1 Hz, 1H), 8.28 (t, J=8.1 Hz, 1H), 8.48 (d, J=8.1 Hz, 1H), 8.56 (d, J=2.0 Hz, 2H), 8.60 (d, J=1.8 Hz, 1H), 8.69 (d, J=2.0 Hz, 1H), 9.04 (s, 1H), 11.33 (brs, 1H), 11.67 (brs, 1H).

EXAMPLE 4

Production of N-(3-chlorophenyl)-2-cyano-3-(3-chloro-4, 5-dihydroxyphenyl) propenamide (Compound No. 4 in Table 1):

Demethylation was effected in the same manner as in Example 2 by using N-(3-chlorophenyl)-2-cyano-3-(3-chloro-4-hydroxy-5-methoxyphenyl) propenamide (587 mg, 1.62 mmol) and 1M solution of boron tribromide in methylene chloride. The resulting solid was suspended in ethanol, refluxed for 10 minutes, allowed to cool to room temperature and filtered to give the objective N-(3-chlorophenyl)-2-cyano-3-(3-chloro-4, 5-dihydroxyphenyl)propenamide (250 mg, 44% in yield).

mp. >300° C.

$^1$HNMR (DMSO-$d_6$, 250 MHz) δ ppm: 7.18 (m, 1H), 7.39 (t, J=8.0 Hz, 1H), 7.45–7.65 (m, 3H), 7.81 (t, J=1.8 Hz, 1H), 8.05 (s, 1H), 10.39 (brs, 1H), 10.49 (brs, 2H).

EXAMPLE 5

Production of N-(3-chlorophenyl)-2-cyano-3-(3-bromo-4-hydroxy-5-methoxyphenyl) propenamide (Compound No. 5 in Table 1):

The reaction was performed in the same manner as in Example 1 with 5-bromovanillin (1.38 g, 5.97 mmol) and N-(3-chlorophenyl) cyanoacetamide (1.16 g, 5.97 mmol) to give the objective N-(3-chlorophenyl)-2-cyano-3-(3-bromo-4-hydroxy-5-methoxyphenyl) propenamide (1.58 g, 65% in yield).

mp. 217°–219° C.

$^1$HNMR (DMSO-$d_6$, 250 MHz) δ ppm: 3.89 (s, 3H), 7.19 (d, J=8.0 Hz, 1H), 7.39 (t, J=8.0 Hz, 1H), 7.60 (d, J=8.0 Hz, 1H), 7.71 (s, 1H), 7.81 (s, 1H), 7.84 (s, 1H), 8.15 (s, 1H), 10.43 (s, 1H), 10.85 (brs, 1H).

EXAMPLE 6

Production of N-(3-chlorophenyl)-2-cyano-3-(3-bromo-4,5-dihydroxyphenyl) propenamide (Compound No. 6 in Table 1):

Demethylation was effected in the same manner as in Example 2 with N-(3-chlorophenyl)-2-cyano-3-(3-bromo-4-hydroxy-5-methoxyphenyl) propenamide (1.38 g, 3.39 mmol) and 1M solution of boron tribromide in methylene chloride (8.5 ml, 8.5 mmol). The resultant solid was mixed with ethanol, refluxed for 10 minutes, allowed to cool to room temperature and filtered to give the objective N-(3-chlorophenyl)-2-cyano-3-(3-bromo-4, 5-dihydroxyphenyl) propenamide (360 mg, 27% in yield).

mp. 266°–270° C.

$^1$HNMR (DMSO-$d_6$, 250 MHz) δ ppm; 7.18 (m, 1H), 7.39 (t, J=8.1 Hz, 7.55–7.68 (m, 7.81 (t, J=1.9 Hz, 1H), 8.05 (s, 10.38 (s, 1H), 10.47 (brs, 1H), 10.59 (brs, 1H).

EXAMPLE 7

Production of N-(3-chlorophenyl)-2-cyano-3-(3-fluoro-4-hydroxy-5-methoxyphenyl) propenamide (Compound No. 7 in Table 1):

The reaction was effected in the same manner as in Example 1 with 5-fluorovanillin (410 mg, 2.41 mmol) and N-(3-chlorophenyl) cyanoacetamide (469 mg, 2.41 mmol) to give the objective N-(3-chlorophenyl)-2-cyano-3-(3-fluoro-4-hydroxy-5-methoxyphenyl) propenamide (476 mg, 57% in yield) as yellow powders.

mp. 235 ° C.

$^1$HNMR (DMSO-$d_6$, 250 MHz) δ ppm: 3.88 (s, 3H), 7.20 (m, 1H), 7.40 (t, J=8.1 Hz, 2H), 7.52–7.63 (m, 3H), 7.83 (t, J=1.8 Hz, 1H), 8.18 (s, 1H), 10.48 (s, 1H)

EXAMPLE 8

Production of N-(3-chlorophenyl)-2-cyano-3-(3-fluoro-4, 5-dihydroxyphenyl) propenamide (Compound No. 8 in Table 1):

Demethylation was effected in the same as in Example 2 with N-(3-chlorophenyl)-2-cyano-3-(3-fluoro-4-hydroxy-5-methoxyphenyl) propenamide (470 mg, 1.36 mmol) and 1M solution of boron tribromide in methylene chloride (3.50 ml, 34.50 mmol). The resulting solid was recrystallized from ethanol-water to give the objective N-(3-chlorophenyl)-2-cyano-3-(3-fluoro-4, 5-dihydroxyphenyl) propenamide (160 mg, 35% in yield) as yellow powder.

mp. 269°–270° C.

$^1$HNMR (DMSO-$d_6$, 250 MHz) δ ppm: 7.20 (m, 1H), 7.34–7.46 (m, 3H), 7.60 (m, 1H), 7.82 (t, J=1.8 Hz, 1H), 8.06 (s, 1H), 10.42 (s, 1H).

EXAMPLE 9

Production of N-(3-chlorophenyl)-2-cyano-3-(2, 3-dibromo-4, 5-dihydroxyphenyl) propenamide (Compound No. 9 in Table 1):

The reaction was effected in the same manner as in Example 1 with 3, 4-dihydroxy-5, 6-dibromobenzaldehyde (1.01 g, 3.41 mmol) and N-(3-chlorophenyl) cyanoacetalmide (644 mg, 3.41 mmol) to give the objective N-(3-chlorophenyl)-2-cyano-3-(2, 3-dibromo-4, 5-dihydroxyphenyl) propenamide (1.26 g, 78% in yield) as yellow needles.

mp. 260°–265 ° C. (dec.)

$^1$HNMR (DMSO-$d_6$, 250 MHz) δ ppm: 7.22 (m, 1H), 7.41 (t, J=8.1 Hz, 1H), 7.62 (m, 1H), 7.66 (s, 1H), 7.84 (t, J= 1.9 Hz, 1H), 8.35 (s, 1H), 10.54 (s, 1H), 10.81 (brs, 2H).

IR (KBr) cm$^{-1}$: 3420, 3300, 3220, 2220, 1660, 1580, 1515, 1455, 1262, 1195, 774.

EXAMPLE 10

Production of N-(4-bromophenyl)-2-cyano-3-(3, 4-dihydroxyphenyl) propenamide (Compound No. 10 in Table 1):

To 2N aqueous sodium hydroxide solution (175 ml, 350 mmol) heated at 60° C. were added cyanoacetic acid (7.2 g, 86.7 mmol) and 3, 4-dihydroxybenzaldehyde (12.0 g, 86.9 mmol), and the resulting mixture was stirred for 30 minutes. The reaction mixture was allowed to cool at room temperature and gradually mixed with dilute hydrochloric acid until the reaction mixture became acidic. The product was filtered and dried to give α-cyano-3, 4-dihydroxycinnamic acid (hereinafter referred to as "Compound A") (10.0 g, 56% in yield).

A mixture of the resulting compound A (400 mg, 1.9 mmol) and a solution of p-bromoaniline (654 mg, 3.8 mmol) in tetrahydrofuran (20 ml) was stirred in ice bath. Triethylamine (0.3 ml, 2.2 mmol) and phosphoryl oxychloride (0.8 ml, 8.6 mmol) were added to the mixture, which was stirred at room temperature for 4 hours. The reaction mixture was concentrated in vacuo to remove the solvent, and the residue was partitioned between water and ethylacetate. The organic layer was separated, dried and concentrated. The residue was recrystallized from ethanol to give the objective N-(4-bromophenyl)-2-cyano-3-(3, 4-dihydroxyphenyl) propenamide (250 mg, 36% in yield).

mp. 277°–278° C.

$^1$HNMR (DMSO-$d_6$, 250 MHz) δ ppm: 6.90 (d, J=8.3 Hz, 1H), 7.33 (dd, J=2.0, 8.3 Hz, 1H), 7.53 (d, J=8.9 Hz, 2H), 7.58 (d, J=2.0 Hz, 1H), 7.63 (d, J=8.9 Hz, 2H), 8.03 (s, 1H), 9.50 (brs, 2H), 10.29 (s, 1H).

EXAMPLE 11

Production of N-(3-bromophenyl)-2-cyano-3-(3, 4-dihydroxyphenyl) propenamide (Compound No. 11 in Table 1):

Condensation of Compound A (996 mg, 4,85 mmol) and m-bromoaniline (0.63 ml, 5.82 mmol) was effected in the same manner as in Example 10. The resulting solid was recrystallized from ethanol-water to give the objective N-(3-bromophenyl)-2-cyano-3-(3, 4-dihydroxyphenyl) propenamide (300 mg, 17% in yield).

$^1$HNMR (DMSO-$d_6$, 250 MHz) δ ppm: 6.91 (d, J=8.3 Hz, 1H), 7.20–7.40 (m, 3H), 7.58 (d, J=2.3 Hz, 1H), 7.60–7.70 (m, 1H), 7.95 (s, 1H), 8.05 (s, 1H), 9.63 (brs, 1H), 10.22 (brs, 1H), 10.32 (brs, 1H).

EXAMPLE 12

Production of N-(4-chlorophenyl)-2-cyano-3-(3, 4-dihydroxyphenyl) propenamide (Compound No. 12 in Table 1):

Condensation of Compound A (400 mg, 1.9 mmol) and p-chloroaniline (482 mg, 3.8 mmol) was effected in the same manner as in Example 10. The resulting solid was recrystallized from ethanol to give the objective N-(4-chlorophenyl)- 2-cyano-3-(3, 4-dihydroxyphenyl) propenamide (110 mg, 18% in yield).

mp. 290° C.

$^1$HNMR (DMSO-$d_6$, 250 MHz) δ ppm: 6.89 (d, J=8.3 Hz, 1H), 7.33 (dd, J=1.8, 8.3 Hz, 1H), 7.40 (d, J=9.0 Hz, 2H), 7.58 (d, J=1.8 Hz, 1H), 7.68 (d, J=9.0 Hz, 2H), 8.03 (s, 1H), 9.85 (brs, 3H), 10.29 (brs. 3H).

EXAMPLE 13

Production of N-(3-chlorophenyl)-2-cyano-3-(3, 4-dihydroxyphenyl) propenamide (Compound No. 13 in Table 1):

Condensation of Compound A (400 mg, 1.9 mmol) and m-chloroaniline (482 mg, 3.8 mmol) was effected in the same manner as in Example 10. The resulting solid was suspended in diethyl ether and refluxed for 10 minutes. The precipitate obtained was filtered to give the objective N-(3-chlorophenyl)-2-cyano-3-(3, 4-dihydroxyphenyl) propenamide (280 mg, 46% in yield).

$^1$HNMR (DMSO-$d_6$, 250 MHz) δ ppm: 6.90 (d, J=8.3 Hz, 1H), 7.17 (dd, J=8.0, 1.9 Hz, 1H), 7.34 (dd, J=2.0, 8.3 Hz, 1H), 7.37 (t, J=8.0 Hz, 1H), 7.53–7.65 (m, 2H), 7.81 (t, J=1.9 Hz, 1H), 8.04 (s, 1H), 9.92 (brs, 3H), 10.33 (brs, 3H).

EXAMPLE 14

Production of N-(3-methylphenyl)-2-cyano-3-(3, 4-dihydroxyphenyl) propenamide (Compound No. 14 in Table 1):

condensation of Compound A (400 mg, 1.9 mmol) and m-toluidine (418 mg, 3.8 mmol) was effected in the same manner as in Example 10. The resulting solid was suspended in hexane-ether (5:1) and refluxed for 10 minutes. The resulting solid was filtered to give the objective N-(3-methylphenyl)- 2-cyano-3-(3, 4-dihydroxyphenyl) propenamide (360 mg, 64% in yield).

$^1$HNMR (DMSO-$d_6$, 250 MHz) δ ppm: 2.29 (s, 3H), 6.86– 6.95 (m, 2H), 7.22 (t, J=7.6 Hz, 1H), 7.32 (dd, J=2.0, 8.3 Hz, 1H), 7.40–7.50 (m, 2H), 7.57 (d, J=2.0 Hz, 1H), 8.01 (s, 1H), 9.61 (s, 1H), 10.09 (s, 1H), 10.17 (s, 1H).

EXAMPLE 15

Production of N-(3-chlorophenyl)-2-cyano-3-(3-cyano-4, 5-dihydroxyphenyl) propenamide (Compound No. 15 in Table 1):

Condensation of 3-cyano-4, 5-dimethoxybenzaldehyde (200 mg, 1.05 mmol) and N-(3-chlorophenyl) cyanoacetacide (204 mg, 1.05 mmol) was effected in the same manner as in Example 1 to give a condensate (140 mg). This was treated with 1M solution of boron tribromide in methylene chloride in the same manner as in Example 2, and the resulting solid was recrystallized from ethanol-water to give the objective N-(3-chlorophenyl)-2-cyano-3-(3-cyano-4, 5-dihydroxyphenyl) propenamide (70 rag, 25% in yield) as brown powdery crystals.

mp. 236°–240° C.

$^1$HNMR (DMSO-$d_6$, 250 MHz) δ ppm: 7.19 (d, J=8.0 Hz, 1H), 7.39 (t, J=8.0 Hz, 1H), 7.59 (d, J=8.0 Hz, 1H), 7.66 (s, 1H), 7.81 (s, 1H), 7.85 (s, 1H), 8.09 (s, 1 H), 10.45 (s, 1H), 11.0 (brs, 2H).

EXAMPLE 16

Production of N-(3-chlorophenyl)-2-cyano-3-(4, 5 -dihydroxy-2-nitrophenyl) propenamide (Compound No. 16 in Table 1):

The reaction of 4, 5-dihydroxy-2-nitrobenzaldehyde (185 mg, 1.01 mmol) and N-(3-chlorophenyl) cyanoacetamide (197 mg, 1.01 mmol) was effected in the same manner as in Example 1 to give the objective N-(3-chlorophenyl)-2 -cyano-3-(4, 5-dihydroxy-2-nitrophenyl)propenamide (100 mg, 28% in yield) as brown powdery crystals.

mp. 219°–225° C. (dec.)

$^1$HNMR (DMSO-$d_6$, 500 MHz) δ ppm: 7.21 (s, 2H) , 7.40 (t, J=8.0 Hz, 1H), 7.61 (d, J=8.0 Hz, 1H), 7.67 (s, 1H), 7.84 (s, 1H), 8.56 (s, 1H), ! 0.5 (brs, 1H).

IR (KBr) cm$^{-1}$: 3330, 3200, 2230, 1665, 1600, 1530, 1450, 1305.

EXAMPLE 17

Production of N-(3-chlorophenyl)-2-cyano-3-[4-hydroxy-3-methoxy-5-(methylsulfonyl) phenyl]propenamide (Compound No. 17 in Table 1):

A solution of 4-hydroxy-3-methoxy-5-(methylsulfonyl) benzaldehyde (345 mg, 1.50 mmol), N-(3-chlorophenyl)cyanoacetamide (292 mg, 1.50 mmol), acetic acid (50 μl) and piperidine (50 μl) in benzene (10 ml) was refluxed for 4 hours under dehydrating with Dean Stark's dehydrating apparatus. The resulting solid was filtered and recrystallized from ethanol to give N-(3-chlorophenyl)-2-cyano-3-[4-hydroxy-3-methoxy-5-(methylsulfonyl) phenyl]propenamide (410 mg, 67% in yield) as yellow powder.

mp. 232°–234 °C.

$^1$HNMR (DMSO-$d_6$, 250 MHz) δ ppm: 3.29 (s, 3H), 3.93 (s, 3H), 7.20 (m, 1H), 7.41 (t, J=8.1 Hz, 1H), 7.62 (m, 1H), 7.84 (t, J=1.9 Hz, 1H), 7.96 (d, J=2.0 Hz, 1H), 8.04 (d, J=2.0 Hz, 1H), 8.29 (s, 1H), 0.43 (s, 1H).

EXAMPLE 18

Production of 2-cyano-3-oxo-3-phenyl-1-(2, 3-dibromo-4, 5-dihydroxy) propene (Compound No. 18 in Table 1):

The reaction of 5, 6-dibromo-3, 4-dihydroxybenzaldehyde (480 mg, 1.62 mmol) and benzoylacetonitrile (235 mg, 1.62 mmol) was effected in the same manner as in Example 1, and the resultant solid was recrystallized from ethanol-water to give the objective 2-cyano-3-oxo-3-phenyl-1-(2, 3-dibromo-4, 5-dihydroxy) propene (365 mg, 53% in yield).

mp. 229°–231 °C. (dec.)

$^1$HNMR (DMSO-$d_6$, 500 MHz) δ ppm: 7.58 (t, J=7.6 Hz, 2H), 7.69 (t, J=7.6 Hz, 1H), 7.83 (m, 3H), 8.21 (s, 1H), 10.86 (brs, 2H).

EXAMPLE 19

Production of N-(3-chlorophenyl)-2-cyano-3-(3-methoxy-4-hydroxy-5-nitrophenyl) propenamide (Compound No. 95 in Table 1):

The reaction of 5-nitrovanillin (915 mg, 4.6 mmol) and N-(3-chlorophenyl) cyanoacetamide (903 mg, 4.6 mmol) was effected in the same manner as in Example 1 to give the objective titled compound (1.53 g, 88%).

$^1$HNMR (DMSO-$d_6$, 250 MHz) δ ppm: 7.21 (brd, J=7.9 Hz, 1H), 7.41 (t, J=8.2 Hz, 1H), 7.61 (brd, J=8.2 Hz, 1H), 7.83 (t, J=1.9Hz, 1H), 7.86 (d, J=2.0 Hz, 1H), 8.01 (d, J=2.0 Hz, 8. 9 (s, 1H).

mp. 229°–231 °C.

EXAMPLE 20

Production of N-(3-chlorophenyl)-2-cyano-3-(3, 4-dihydroxy-5-nitrophenyl) propenamide (Compound No. 96 in Table 1):

The reaction of N-(3-chlorophenyl)-2-cyano-3-(3-methoxy-4-hydroxy-5-nitrophenyl) propenamide (865 mg, 2.3 mmol) and 1M solution of boron tribromide in methylene chloride (8.0 ml, 8.0 mmol) was effected in the same manner as in Example 2. The resultant solid was suspended in ethanol-water to give the objective titled compound (240 mg, 29%) as coppery yellow powder.

$^1$HNMR (DMSO-$d_6$, 250 MHz) δ ppm: 3.95 (s, 3H), 7.21 (ddd, J=0.8, 1.9, 8.1 Hz, 1H), 7.41 (t, J=8.1 Hz, 1H), 7.62 (dt, J=8.1, 0.9 7.83 (t, J=1.9 Hz, 1H), 7.94 (d, J= 1.9 Hz, 1H), 8.19 (d, 1.9 Hz, 1H), 8.27 (s, 1H), 10.52 (s, 1H)

mp. 242°–248° C. (dec.)

EXAMPLE 21

Production of N-(3-chlorophenyl)-2-cyano-3-[3-methoxy-4-hydroxy-5-(trifluoromethyl) ]propenamide (Compound No. 97 in Table 1):

Condensation of 3-methoxy-4-hydroxy-5-(trifhoromethyl) benzaldehyde (770 mg, 3.5 mmol) and N-(3-chlorophenyl) cyanoacetamide (680 mg, 3.5 mmol) was effected in the same manner as in Example 1 to give the objective titled compound (956 mg, 76%).

$^1$HNMR (DMSO-$d_6$, 250 MHz) δ ppm: 3.93 (s, 3H), 7.19 (m, 1H), 7.39 (t, J=8.1 Hz, 1H), 7.60 (m, 1H), 7.82 (t, J= 1.9 Hz, 1H), 7.87 (d, J=1.7 Hz, 1H), 7.93 (1.7 Hz, 1H), 8.26 (s, 1H), 10.47 (s, 1H), 11.21 (brs, 1H).

mp. 200°–205 °C.

EXAMPLE 22

N-(3-chlorophenyl)-2-cyano-3-[3, 4-dihydroxy-5-(trifhoromethyl) phenyl ]propenamide (Compound No. 98 in Table 1):

Reaction of N-(3-chlorophenyl)-2-cyano-[3-methoxy-4-hydroxy-5-(trifluoromethyl)]propenamide obtained in Example 21 and 1M solution of boron tribromide in methylene chloride (4.9 ml, 4.9 mmol) was effected in the same manner as in Example 2 to give the objective titled compound (576 mg, 52%).

$^1$HNMR (DMSO-$d_6$, 250 M Hz) δ ppm: 7.18 (m, 1H), 7.38 (t, J=8.1 Hz, 1H), 7.60 (brd, J=8.1 Hz, v.65 (d, J= 1.8 Hz, 1H), 7.81 (t, J=1.8 Hz, 1H), 7.86 (d, J=1.8 Hz, 1H), 8.17 (s, 1H), 104.1 (s, 1H), 10.87 (brs, 1H).

mp. 247°–2500° C.

EXAMPLE 23

Production of N-(3-chlorophenyl)-2-cyano-3-(2, 5-difluoro-3, 4-dihydroxyphenyl) propenamide (Compound No. 20 in Table 1):

1, 4-Difluoro-2-methoxy-3-hydroxybenzene (1.60 g, 9.99 mmol) was converted into 2, 5-difluoro-2-methoxy-3-hydroxybenzene (610 mg, 33%) according to the method as described in L. Kirk et al., J. Org. Chem., 51, 4073 (1986). This compound (350 mg, 1.86 mmol) was allowed to react with 1M solution of boron tribromide in methylene chloride in the same manner as in Example 2. The crude product obtained above was dissolved in methylene chloride (2 ml), and diisopropylethylamine (0.4 ml, 2.3 mmol) and methoxymethyl chloride (0.45 ml, 6.0 mmol) were added to the solution, which was stirred at room temperature for 1 hour. The reaction mixture was mixed with water, extracted with ethyl acetate-hexane and the extract was concentrated in vacuo. The residue was chromatographed on a column of silica gel to give 2, 5-difluoro-3, 4-bis (methoxymethyloxy) benzaldehyde (200 mg, 41%).

A solution of the aldehyde (97 mg, 0.37 mmol) obtained above, N-(3-chlorophenyl) acetanilide (72 mg, 0.37 mmol) and piperidine (3 μl) in ethanol (2 ml) was refluxed for 2 hours. The mixture was mixed with 3 N aqueous hydrochloric acid (0.5 ml), refluxed for 30 minutes, allowed to cool to room temperature and the resultant crystals were filtered to give the titled compound (52 mg, 41%) as yellow powders.

$^1$HNMR (DMSO-$d_6$, 250 MHz) δ ppm: 7.21 (m, 1H), 7.40 (t, J=8.1 Hz, 1H), 7.53–7.65 (m, 2H), 7.83 (t, J=2.0 Hz, 1H), 8.24 (s, 1H), 0.55 (S, 1H), 10.70 (brs, 1H).

MP. 255°–262° C. (dec.)

EXAMPLE 24

Production of 2-cyano-3-(2, 5-difluoro-3, 4-dihydroxyphenyl) propenanilide (Compound No. 99 in Table 1):

The aldehyde, 2, 5-difluoro-3, 4-bis (methoxymethyloxy) benzaldehyde (115 mg, 0.44 mmol) obtained above was allowed to react with cyanoacetanilide (70 mg, 0.44 mmol)

in the same manner as in Example 22 to give the objective titled compound (52 mg, 36%) as yellow powders.

¹HNMR (DMSO-d₆, 250 MHz) δ ppm: 7.14 (t, J=7.3 Hz, 1H), 7.37 (t, J=7.6 Hz, 2H), 7.57 (dd, J=6.2, 11.6 Hz, 1H), 7.66 (d, J=8.2 Hz, 1H), 8.22 (s, 1H), 10.39 (s, 1H), 10.7 (brs, 2H).

mp. 261° C. (dec.)

EXAMPLES 25–41

The following products were produced from the corresponding starting compounds in the same manner as in Example 1. Table 6 shows the yields and physical data.

TABLE 6

| Example No. (Compound No.) | Method* | Yield (%) | ¹HNMR | mp. (°C.) |
|---|---|---|---|---|
| 25 (23) | 1 | 72 | ¹HNMR(DMSO-d₆, 250MHz)δ ppm; 2.22(S, 6H), 7.17(m, 1H), 7.38(t, J=8.1Hz, 1H), 7.60(m, 1H), 7.68(brs, 2H), 7.82(t, J=1.9Hz, 1H), 8.07(s, 1H), 9.54(S, 1H), 10.34(S, 1H). | 246–248 |
| 26 (100) | 1 | 34 | ¹HNMR(DMSO-d₆, 250MHz)δ ppm; 7.19(m, 1H), 7.39(t, J=8.1Hz, 1H), 7.59(d, J=8.1Hz, 1H)7.81(t, J=1.8 Hz, 1H), 8.15(S, 1H), 8.23(S, 2H), 10.47(S, 1H). | 287–288 |
| 27 (101) | 1 | 73 | ¹HNMR(DMSO-d₆, 250MHz)δ ppm; 2.18(S, 3H), 3.85(S, 3H), 7.18(m, 1H), 7.38(t, J=8.1Hz, 1H), 7.46(brs, 1H), 7.56–7.63(m, 2H), 7.82(t)J=1.6Hz, 1H), 8.12 (S, 1H), 9.90(S, 1H), 10.37(S, 1H). | 167–169 |
| 28 (102) | 1 | 26 | ¹HNMR(DMSO-d₆, 250MHz)δ ppm; 7.18(m, 2H), 7.39(t, J= 8.1Hz, 1H), 7.60(d, J=8.1Hz, 1H), 7.82(S, 1H), 8.17(dd, J=2.0, 8.8Hz, 1H), 8.27(S, 1H), 8.54(d, J= 2.0Hz, 1H), 10.46(S, 1H). | 265–268 |
| 29 (103) | 1 | 60 | ¹HNMR(CBCl₃-DMSO-d₆ (5:1), 250MHz)δ ppm; 6.98(d, J= 8.3Hz, 1H), 7.10(m, 1H), 7.28(t, J=8.2Hz, 1H), 7.42(dd, J=2.1, 8.3Hz, 1H), 7.59(m, 1H), 7.75(d, J= 2.1Hz, 1H), 7.85(t, J=2.0Hz, 1H), 8.15(S, 1H), 9.64(S, 1H). | 194–196 |
| 30 (104) | 1 | 84 | ¹HNMR(DMSO-d₆, 250MHz)δ ppm; 7.15–7.25(m, 2H), 7.40 (t, J=8.1Hz, 1H), 7.61(m, 1H), 7.83(t, J=1.9Hz, 1H), 7.89(dd, J=2.1, 8.6Hz, 1H), 8.09(d, J=2.1 Hz, 1H), 8.17(S, 1H), 10.44(S, 1H), 11.50(brs, 1H). | 265–267 |
| 31 (105) | 1 | 63 | ¹HNMR(DMSO-d₆, 250MHz)δ ppm; 3.89(S, 3H), 7.12(t, J= 7.4Hz, 1H), 7.36(t, J=7.5Hz, 2H), 7.65(d, J= 7.5Hz, 2H), 7.71(d, J=1.8Hz, 1H), 7.84(d, J=1.8 Hz, 1H), 8.14(S, 1H), 10.26(S, 1H), 10.77(brs, 1H). | 241–243 |
| 32 (106) | 1 | 70 | ¹HNMR(DMSO-d₆, 200MHz)δ ppm; 3.88(S, 3H), 7.15(t, J= 7.0CHz, 1H), 7.37(t, J=7.0Hz, 2H), 7.56(m, 2H), 7.66(d, J=7.0Hz, 2H), 8.16(S, 1H), 10.30(brs, 1H). | 234–235 |
| 33 (107) | 1 | 47 | ¹HNMR(DMSO-d₆, 250MHz)δ ppm; 6.90(d, J=8.4Hz, 1H), 7.41(dd, J=2.2, 8.4Hz, 1H), 7.57(dd, J=7.2, 8.9 Hz, 1H), 7.68–7.81(m, 4H), 7.92(S, 1H), 10.10(brs, 1H). | — |
| 34 (108) | 1 | 91 | ¹HNMR(DMSO-d₆, 250MHz)δ ppm; 6.89(d, J=8.3Hz, 1H), 7.40(dd, J=2.2, 8.3Hz, 1H), 7.62(d, J=8.5Hz, 2H), 7.70(d, J=2.1Hz, 1H), 7.79(d, J=8.5Hz, 2H), 7.92(S, 1H), 10.05(brs, 2H) | 205–209 (Analyze) |
| 35 (42) | 10 | 49 | ¹HNMR(DMSO-d₆, 250MHz)δ ppm; 6.91(d, J=8.3Hz, 1H), 7.36(dd, J=2.2, 8.2Hz, 1H), 7.60(d, J=2.2Hz, 1H), 7.65(t, J=8.2Hz, 1H), 7.97(J=2.2, 8.2Hz, 1H), 8.05–8.15(m, 2H), 8.64(t, J=2.2Hz, 1H), 9.95 (brs, 2H), 10.65(S, 1H). | 291–292 |
| 36 (43) | 10 | 43 | ¹HNMR(DMSO-d₆, 250MHz)δ ppm; 6.91(d, J=8.3Hz, 1H), 7.35(brd, J=8.0Hz, 1H), 7.50–7.65(m, 3H), 7.93 (m, 1H), 8.00–8.15(m, 2H), 9.94 and 10.48(brs, 3H). | >300 |
| 37 (109) | 10 | 24 | ¹HNMR(DMSO-d₆, 250MHz)δ ppm; 6.85–7.00(m, 2H), 7.30–7.50(m, 3H), 7.55–7.65(m, 2H), 8.04(S, 1H), 9.80 and 10.36(brs, 3H). | 268–270 |
| 38 (110) | 2 | 18 | ¹HNMR(DMSO-d₆, 250MHz)δ ppm; 2.15(S, 3H), 7.17(m, 1H), 7.24(d, J=1.8Hz, 1H), 7.38(t, J=8.1Hz; 1H), 7.53(d, J=1.8Hz, 1H), 7.59(m, 1H), 7.82(t, J=1.9 Hz, 1H), 8.01(S, 1H), 9.58, 10.02 and 10.32(each S, each 1H). | 268–270 |
| 39 (111) | 2 | 46 | ¹HNMR(DMSO-d₆, 200MHz)δ ppm; 7.13(t, J=6.0Hz, 1H), 7.30–7.50(m, 4H), 7.66(d, J=6.0Hz, 2H), 8.06(S, 1H), 10.27(brs, 3H). | 268–268.5 |
| 40 (112) | 2 | 61 | ¹HNMR(DMSO-d₆, 250MHz)δ ppm; 7.12(t, J=7.3Hz, 1H), 7.35(t, J=7.9Hz, 2H), 7.55–7.70(m, 4H), 8.04(S, 1H), 10.22(S, 1H), 10.43 and 10.57(each brs, each 1H). | 265–267 |
| 41 (113) | 1, 2 | 44 | ¹HNMR(DMSO-d₆, 500MHz)δ ppm; 4.41(d, J=6.0Hz, 2H), 7.20–7.40(m, 5H)7.51(M, 2H), 8.10(S, 1H), 5.7(t, J=6.0Hz, 1H), 10.48(brs, 1H). | 180–184 |

Method*: The numerals in the column corresponds to the number of Example wherein synthetic method for preparing the compound is described.

EXAMPLE 42

Production of N-(3-chlorophenyl)-2-cyano-3-(3-butoxy-4-hydroxy-5-fluorophenyl) propenamide (Compound No. 114);

To a suspension of sodium hydride (688 mg, 28.7 mmol) in dimethylformamide (20 ml) on ice bath was bit by bit added 3-fluorosalicylaldehyde (2.68 g, 19.1 mmol) with stirring. After dropwise adding benzyl bromide (2.73 ml, 22.9 mmol), the mixture was stirred under ice cooling for 30 minutes, stirred at room temperature for 2 hours, mixed with water and the product was shaken with diethyl ether (60 ml×2). The extracts were washed with 10% aqueous sodium carbonate solution, dilute hydrochloric acid and water in this order, dried over anhydrous magnesium sulfate and concentrated in vacuo to remove the solvent to give 2-benzyloxy-3-fluorobenzaldehyde as an oily material.

To a solution of this aldehyde in methylene chloride (50 ml) was added m-chloroperbenzoic acid (5.08 g, 25.0 mmol, 85% purity) with ice cooling, and the resulting mixture was stirred at the same temperature for 2 hours, allowed to warm to room temperature and stirred overnight. The reaction mixture was mixed with saturated aqueous sodium bicarbonate solution and hexane-ethyl acetate mixture and stirred, and the organic layer was separated. The organic layer was washed with saturated aqueous sodium bicarbonate solution and water in this order, dried over anhydrous magnesium sulfate and concentrated in vacuo. The resulting residue was dissolved in methanol (20 ml), and the solution was mixed with potassium carbonate (4.14 g, 30.0 mmol) under ice cooling. The mixture was stirred at room temperature for 2 hours, acidified with dilute hydrochloric acid and extracted with ethyl acetate (50 ml× 2). The extracts were washed with saturated aqueous brine, dried over anhydrous magnesium sulfate and concentrated. The residue was chromatographed on a column of silica gel 10 to give 2-benzyloxy-3-fluorophenol (1.60 g, 38%). A solution of the phenol (540 mg, 2.47 mmol) obtained above, potassium carbonate (681 mg, 4.95 mmol), butyl bromide (0.4 ml, 3.71 mmol) and potassium iodide (616 mg, 3.71 mmol) in dimethylformamide (40 ml) was stirred at 100° C. for 1.5 hours. The reaction mixture was poured onto ice water, acidified with dilute hydrochloric acid and extracted with diethyl ether (50 ml x 2). The extracts were washed with 10% aqueous sodium carbonate solution and water in this order, dried over anhydrous magnesium sulfate and concentrated. The resulting residue was chromatographed on a column of silica gel to give 1-benzyloxy-2-butoxy-3-fluorobenzene (590 mg, 87%) as an oily material.

This oily material was dissolved in ethanol (3 ml), mixed with 5% palladium carbon (70 mg) and hydrogenated at room temperature for 2 hours. The reaction mixture was filtered, and the filtrate was concentrated in vacuo to give 2-butoxy-6-fluorophenol.

The above phenol was added to a mixture of 50% aqueous dimethylamine (360 mg), 37% aqueous formaldehyde (325 mg) and ethanol (1.5 ml) and refluxed for 3 hours. The reaction mixture was concentrated in vacuo, and the residue was dissolved in chloroform (4 ml). Methyl iodide (2 ml) was added to the solution, which was stirred at room temperature for 2 hours and concentrated in vacuo. The residue was mixed with acetic acid (2 ml), water (2 ml) and hexamethylenetetramine (520 mg, 3.71 mmol), stirred at 120° C. (oil bath temperature) for 3 hours, mixed with conc. hydrochloric acid (2 ml), refluxed for 10 minutes and allowed to cool to room temperature. After adding water, the reaction mixture was extracted with diethyl ether (30 ml×1, 20 ml×1). The extracts were washed with water (30 ml), dried over anhydrous magnesium sulfate and concentrated to give 3-butoxy-4-hydroxy-5-fluorobenzaldehyde (380 mg, 72% in overall yield from 2-benzyloxy-3-fluorophenol).

The above aldehyde (148 mg, 0.7 mmol) was allowed to condense with N-(3-chlorophenyl)cyanoacetamide (136 mg, 0.7 mmol) in the same manner as in Example 1 to give the objective N-(3-chlorophenyl)-2-cyano-3-(3-butoxy-4-hydroxy- 5-fluorophenyl) propenamide (94 mg, 34%).

$^1$HNMR (CDCl$_3$, 250 MHz) δ ppm: 1.01 (t, J=7.3 Hz, 3H), 1.53 (m, 2H), 1.87 (m, 2H), 4.16 (t, J=6.5 Hz, 2H), 7.18 (ddd, J=1.0, 1.6, 7.8 Hz, 1H), 7.31 (t, J=8.0 Hz, 1H), 7.39 (dd, J=2.0 10.7 Hz, 1H), 7.41–7.47 (m, 2H), 7.77 (t, J=2.0 Hz, 1H), 7.94 (brs, 1H), 8.26 (s, 1H). mp. 183°–185° C.

EXAMPLE 43

Production of 2-cyano-3-(3-butoxy-4-hydroxy-5-fluorophenyl) propenanilide (Compound No. 115):

Condensation of 3-butoxy-4-hydroxy-5-fluorobenzaldehyde (324 mg, 1.53 mmol) obtained in Example 42 and cyanoacetanilide (245 mg, 1.53 mmol) was effected in the same manner as in Example 1 to give the titled compound (300 mg, 58%).

$^1$HNMR (DMSO-d$_6$, 250 MHz) δ ppm: 0.95 (t, J=7.4 Hz, 3H), 1.47 (m, 2H), 1.77 (m, 2H), 4.07 (t, J=6.66 Hz, 2H), 7.14 (t, J=7.3 Hz, 1H), 7.37 (t, J=7.9 Hz, 2H), 7.50– 7.60 (m, 2H), 7.67 (d, J=7.5 Hz, 2H), 8.15 (s, 10.3 (s, 1H), 10.45 (brs, 1H).

mp. 177°–179° C.

EXAMPLE 44

Production of N-(3-chlorophenyl)-2-cyano-3-[3-fluoro-4-hydroxy-5- (1-methylethyl) oxyphenyl]propenamide (Compound No. 116):

Alkylation of 2-benzyloxy-3-fluorophenol (1.05 g, 4.81 mmol) obtained in Example 42 was effected with isopropyl iodide (0.96 ml, 9.62 mmol) and potassium carbonate (1.66 g, 12.0 mmol) in the same manner as in Example 42, followed by debenzylation and formylation. Thus, 3-fluoro-4 -hydroxy-5-(1-methylethyl) oxybenzaldehyde (325 mg, 34% in overall yield) was obtained.

The above aldehyde (149 mg, 0.75 mmol) was allowed to condense with N-(3-chlorophenyl) cyanoacetamide (146 mg, 0.75 mmol) to give the objective titled compound (185 mg, 69%) as light yellow needles.

$^1$HNMR (DMSO-d$_6$, 250 MHz) δ ppm: 1.34 (d, J=6.0 Hz, 6H), 4.60 (sep, J=6.0 Hz, 1H), 7.20 (m, 1H), 7.40 (t, J= 8.1 Hz, 1H), 7.49–7.64 (m, 3H), 7.83 (t, J=1.8 Hz, 1H), 8.16 (s, 1H), 10.37 and 10.47 (each s, 2H).

mp. 181°–183° C.

EXAMPLE 45

Production of 2-cyano-3-[3-fluoro-4-hydroxy-5-(1-methylethyl )oxyphenyl ]propenanilide (Compound No. 117):

Condensation of 3-fluoro-4-hydroxy-5-(1-methylethyl) oxybenzaldehyde (168 mg, 0.85 mmol) obtained in the foregoing Example with cyanoacetanilide (136 mg, 0.85 mmol) in the same manner as in Example 1 to give the objective titled compound (180 mg, 60%) as yellow powdery crystals.

$^1$HNMR (CDCl$_3$, 250 MHz) δ ppm: 1.29 (d, J=6.1 Hz, 6H), 4.70 (sep. J=6.1 Hz, 1H), 7.20 (t, J=7.5 Hz, 1H), 7.30–7.52 (m, 2H), 7.39 (t, J=7.5 Hz, 2H), 7.62 (d, J= 7.5 Hz, 2H), 7.97 (brs, 1H), 8.26 (s, 1H).

mp. 156°–157° C.

EXAMPLE 46

Production of N-(3-chlorophenyl)-2-cyano-3-(3-butoxy-4-hydroxyphenyl) propenamide (Compound No. 118):

To a solution of 4-bromophenol (7.21 g, 41.6 mmol) in acetic anhydride (25 ml) was added 4 drops of conc. sulfuric acid, and the mixture was stirred at 90° C. for 1.5 hours. Ice water was added to the mixture, which was extracted with ethyl acetate (60 ml×1; 30 ml×1). The extracts were washed with saturated aqueous sodium bicarbonate solution and water in this order, dried over anhydrous magnesium sulfate and concentrated in vacuo to give 4-bromoacetoxybenzene (8.96 g, quantitatively).

Anhydrous aluminum chloride (11.03 g, 82.8 mmol) was added bit by bit to 4-bromoacetoxybenzene (8.90 g, 41.4 mmol) heated at 80° C. with stirring. The mixture was stirred at 100° C. for 2.5 hours, allowed to cool, mixed bit by bit with ice water and extracted with ethyl acetate (80 ml×1; 20 ml×1). The extract was dried over anhydrous magnesium sulfate and concentrated to give 2-acetyl-4-bromophenol (7.92 g, 89%).

To a solution of 2-acetyl-4-bromophenol (3.63 g, 16.9 mmol) in methylene chloride (20 ml) on ice bath were added diisopropylethylamine (5.88 ml, 33.8 mmol) and chloromethyl methyl ether (1.92 ml, 25.3 mmol) with stirring. The mixture was stirred at room temperature overnight, poured into water and extracted with ethyl acetate. The extract was dried over anhydrous magnesium sulfate and concentrated to give 4-(methoxymethyl) oxy-3-acetylbromobenzene (4.35 g, quantitatively).

To a solution of the bromobenzene (4.35 g, 16.8 mmol) obtained above in chloroform (50 ml) was added m-chloroperbenzoic acid (4.09 g, 20.2 mmol, 85% purity), and the mixture was refluxed. Five hours later, m-chloroperbenzoic acid (2.05 g, 10.1 mmol) was added, and the mixture was refluxed for 29 hours. The reaction mixture was mixed with saturated aqueous sodium bicarbonate solution and hexane-ethyl acetate, and the organic layer was separated. The organic layer was washed with saturated aqueous sodium bicarbonate solution and water in this order, dried over anhydrous magnesium sulfate and concentrated. The resulting residue was dissolved in methanol (20 ml) and mixed with potassium carbonate (4.64 g, 33.6 mmol) at 5 ° C. Twenty minutes later, the mixture was acidified with 3N HCl and extracted with ethyl acetate. The extract was dried over anhydrous magnesium sulfate and concentrated to give 2-(methoxymethyl) oxy-5-bromophenol (3.33 g, 85%).

To a solution of the bromophenol. (1.02 g, 4.38 mmol) obtained above in dimethylformamide (15 ml) were added potassium carbonate (1.21 g, 8.76 mmol), butyl bromide (0.71 ml, 6.57 mmol) and potassium iodide (1.09 g, 6.57 mmol), and the resulting mixture was stirred at 100° C. with heating. Two hours later, the reaction mixture was poured onto ice water and acidified with dilute hydrochloric acid. The product was extracted with diethyl ether (50 ml×2), and the extract was washed with 10% aqueous sodium carbonate solution and water in this order, dried over anhydrous magnesium sulfate and concentrated. The residue was chromatographed on a column of silica gel to give 3 -butoxy-4-(methoxymethyl) oxybromobenzene (920 mg, 69%) as an oily material.

To a solution of 3-butoxy-4-(methoxymethyl) oxybromobenzene (910 mg, 2.97 mmol) in tetrahydrofuran (15 ml) chilled at −72° C. was dropwise added n-butyllithium (2.22 ml, 3.56 mmol, 1.6M hexane solution) under nitrogen atmosphere, and 20 minutes later dimethylformamide (0.28 ml, 3.62 mmol) was added to the mixture, which was stirred for 30 minutes at the same temperature. The reaction mixture was mixed with water, and the product was extracted with ethyl acetate. The extract was dried over anhydrous magnesium sulfate and concentrated. The residue was chromatographed on a column of silica gel to give 3-butoxy- 4-(methoxymethyl) oxybenzaldehyde (556 mg, 84%).

The benzaldehyde (200 mg, 0.9 mmol) obtained above was allowed to condense with N-(3-chlorophenyl) cyanoacetanilide (175 mg, 0.9 mmol) in the same manner as in Example 1 to give N-(3-chlorophenyl)-2-cyano-3-[3 -butoxy-4-(methoxymethyl) oxyphenyl]propenamide (210 mg, 57%). To a solution of the condensate (140 mg, 0.34 mmol) in ethanol (5 ml) was added 3 N hydrochloric acid (1 ml), and the mixture was stirred at 60° C. for 2 hours with heating. After cooling, the resulting precipitate was filtered to give the objective titled compound (120 mg, 95%) as light yellow needles.

$^1$HNMR (CDCl$_3$, 250 MHz) δ ppm: 1.01 (t, J=7.3 Hz, 3H), 1.40–1.70 (m, 2H), 1.86 (m, 2H), 4.16 (t, J n=6.4 Hz, 2H), 6.27 (s, 1H), 7.03 (d, J=8.3 Hz, 1H), 7.17 (m, 1H), 7.31 (t, J=8.1 Hz, 1H), 7.40–7.50 (m, 2H), 7.70 (d, J=1.9 Hz, 1H), 7.77 (t, J=1.9 Hz, 1H), 7.95 (brs, mp. 154°–156 ° C.

EXAMPLE 47

Production of 2-cyano-3-hydroxy-3-(3, 4-dihydroxyphenyl) propenanilide (Compound No. 119):

To a solution of acetonitrile (2.70 ml, 51.9 mmol) in tetrahydrofuran (60 ml) chilled at −72° C. was dropwise added a solution of 2M solution of lithium diisopropylamide in cyclohexane (22.0 ml, 44.0 mmol), and 30 minutes later a solution of 3, 4-bis (t-butyldimethylsilyloxy) benzaldehyde (12.08 g, 32.95 mmol) in tetrahydrofuran (30 ml) was dropwise added in 15 minutes. After stirring at −72° C. for 30 minutes, the reaction mixture was poured into saturated aqueous ammonium chloride solution, and the product was extracted with ethyl acetate (100 ml×2). The extracts were dried over anhydrous magnesium sulfate and concentrated to give 3-hydroxy-3-[3, 4-bis (t-butyldimethylsilyloxy) phenyl]propionitrile (2.64 g, 6.48 mmol). To a solution of this compound in acetone (200 ml) was dropwise added Jones reagent (10 ml, 40 mmol) in 20 minutes under ice cooling, and the resulting mixture was stirred at room temperature for 20 minutes. To the reaction mixture was added 2-propanol until the reaction mixture turned green, and then water (200 ml) was added. The mixture was extracted with hexane-ethyl acetate (70 ml× 2), and the extract was washed with saturated aqueous brine (100 ml), dried over anhydrous magnesium sulfate and concentrated in vacuo. The crude product was chromatographed on a column of silica gel to give the corresponding ketone, 3-oxo-3-[3, 4-bis (t-butyldimethylsilyloxy) phenyl]propionitrile (7.41 g, 56%) as an oily material.

To a solution of the ketone (4.82 g, 11.89 mmol) in benzene (30 ml) were added triethylamine (2.14 ml, 15.46 mmol) and phenyl isocyanate (1.42 ml, 13.08 mmol) under ice cooling, and the resultant mixture was stirred at room temperature for 20 minutes. The mixture was concentrated in vacuo, and the residue was mixed with water (80 ml) and chloroform (80 ml). The aqueous layer was acidified with dilute hydrochloric acid, and the organic layer was separated. The organic extract was dried over anhydrous magnesium sulfate and concentrated. The residue was recrystallized from hexane-chloroform to give an adduct, 2-cyano-3-hydroxy-3-[3, 4-bis (t-butyldimethylsilyloxy)phenyl] propenanilide (5.15 g, 88%).

To a solution of the adduct (504 mg, 0.96 mmol) in tetrahydrofuran (8 ml) was added a solution of tetrabutyl ammonium fluoride in tetrahydrofuran (2.0 ml, 2.0 mmol, 2 M), and the resulting mixture was stirred for 30 minutes. The mixture was mixed with excessive amount of 3N aqueous hydrochloric acid and water (20 ml), stirred at room temperature for 2 hours and the product was extracted with ethyl acetate (40 ml). The extract was concentrated, and the residue was suspended in diethyl ether and filtered. The residue was dissolved in a mixture of methanol-ethanol, mixed with ion exchange resin Dowex 50 (500 mg), stirred at room temperature for 3 days and the resin was filtered off. The filtrate was concentrated and the residue was recrystallized from ethanol-water to give the objective titled compound (100 mg, 35%).

$^1$HNMR (DMSO-$d_6$, 250 MHz) δ ppm: 6.83 (d, J=8.0 Hz, 1H), 7.11 (t, J=7.3 Hz, 1H), 7.20–7.40 (m, 4H), 7.54 (d, J=7.9 Hz, 2H), 9.50 (brs, 2H), 10.70 (brs, 1H).

mp. 218°–222° C.

EXAMPLE 48

Production of N-(3-chlorophenyl)-2-cyano-3-hydroxy-3-(3,4-dihydroxyphenyl) propenamide (Compound No. 120):

The ketone (1.02 g, 2.52 mmol) obtained in Example 47 was allowed to react with 3-chlorophenyl isocyanate (0.34 ml, 2.77 mmol) in the same manner as in Example 47, followed by desilylation, and the crude product was recrystallized from ethanol-water to give the titled compound (100 mg, 31%).

$^1$HNMR (DMSO-$d_6$, 250 MHz) δ ppm: 6.85 (d, J=8.8 Hz, 1H), 7.19 (d, J=7.5 Hz, 1H), 7.20–7.55 (m, 4H), 9.80 (brs, 3H), 10.63 (brs, 1H).

mp. 235°–237° C.

EXAMPLE 49

Production of N-(3-toluyl)-2-cyano-3-hydroxy-3-(3,4-dihydroxyphenyl) propenamide (Compound No. 121):

Corresponding ketone (1.018 g, 2.51 mmol) was allowed to react with 3-methylphenyl isocyanate (0.36 ml, 2.76 mmol) in the same manner as in Example 48 to give the titled compound (145 mg, 43%).

$^1$HNMR (DMSO-$d_6$, 250 MHz) δ ppm: 2.29 (s, 3H), 6.88 (d, J=8.9 Hz, 1H), 6.98 (d, J=7.3 Hz, 1H), 7.23 (t, J=7.7 Hz, 1H), 7.30–7.42 (m, 4H), 10.15 (s, 2H).

mp. 213°–215° C.

EXAMPLE 50

Production of N-ethyl-2-cyano-3-(3, 4-dihydroxyphenyl)-2-butenanilide (Compound No. 122):

To a solution of 3, 4-dimethoxyacetophenone (5.68 g, 31.53 mmol) and cyanoacetic acid (2.95 g, 34.68 mmol) in benzene were added acetic acid (1.9 ml) and ammonium acetate (150 mg), and the resultant mixture was refluxed with Dean Stark's dehydrating apparatus for 13 hours while adding ammonium acetate (130 mg) every 4 hours. The mixture was mixed with chloroform (200 ml), 2N aqueous sodium hydroxide solution (100 ml) and water (200 ml), stirred well and the aqueous layer was separated. The aqueous layer was acidified with dilute hydrochloric acid, and the resulting precipitate was filtered off. The residue was washed with diethyl ether to give a carboxylic acid, 2-cyano-3-methyl-3-(3, 4-dimethoxyphenyl) propionic acid (2.25 g, 29%).

This carboxylic acid (234 mg, 0.95 mmol) was allowed to condense with N-ethylaniline (138 mg, 1.14 mmol) in the same manner as in Example 10, and then demethylation was effected in the same manner as in Example 2 to give the objective titled compound (226 mg, 80%).

$^1$HNMR (DMSO-$d_6$, 250 MHz) δ ppm: 1.09 (t, J=7.1 Hz, 3H), 2.09 (s, 3H), 3.49 (8, J=7.1 Hz, 2H), 6.40–6.70 (m, 1H), 7.20–7.60 (m, 5H), 9.15 and 9.49 (each brs, each 1H).

mp. 174°–1770° C.

The compounds of the present invention can be prepared easily, and they show more potent tyrosine kinase inhibition than known tyrosine kinase inhibitors, and therefore, they are particularly useful as anticancer agents with less side effects.

What is claimed is;

1. A styrene derivative of the following formula (I):

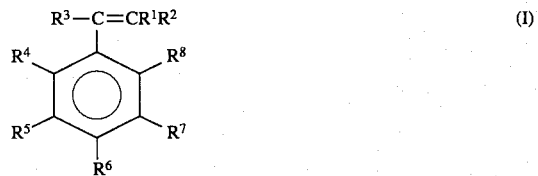

wherein $R^1$ represents a cyano group;

$R^2$ represents —$CONR^9R^{10}$ wherein $R^9$ and $R^{10}$ independently each represent a hydrogen atom or

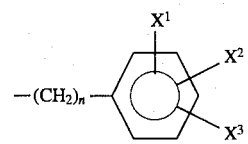

(in which n represents 0 or an integer of from 1 to 5, and $X^1$, $X^2$ and $X^3$ independently each represent a hydrogen atom, halogen atom, $C_1$–$C_5$ alkyl group, $C_1$–$C_5$ alkoxy group, hydroxy group, nitro group or cyano group), with the proviso that $R^9$ and $R^{10}$ don't represent hydrogen atom at the same time;

$R^3$ represents & hydrogen atom, $C_1$–$C_5$ alkyl group or hydroxy group; and $R^4$, $R^5$, $R^6$, $R^7$ and $R^8$ independently each represent (1) a hydrogen atom, (2) hydroxy group, (3) halogen atom, (4) $C_1$–$C_5$ alkoxy group, (5) nitro group, (6) cyano group, (7) —$NR^{12}R^{13}$ wherein $R^{12}$ and $R^{13}$ independently each represent a hydrogen atom, $C_1$–$C_5$ alkyl group or benzoyl group, (8) —$SOpR^{14}$ wherein p represents 0, 1 or 2, and $R^{14}$ represents a $C_1$–$C_5$ alkyl group or phenyl group, (9) —$COR^{15}$ wherein $R^{15}$ represents a hydrogen atom, $C_1$–$C_5$ alkyl group, $C_1$–$C_5$ alkoxy group, hydroxy group, phenyl group, phenoxy group or —$NHR^{16}$ (in which $R^{16}$ represents a $C_1$–$C_5$ alkyl group or phenyl group), or (10) a $C_1$–$C_5$ alkyl group optionally substituted by a halogen atom;

with the proviso that at least one of $R^4$ to $R^8$ is a hydroxy group, and that when $R^3$ is a hydrogen atom and $R^4$ to $R^8$ independently each represent a hydrogen atom, hydroxy group, $C_1$–$C_5$ alkoxy group, —$NR^{12}R^{13}$ (in which $R^{12}$ and $R^{13}$ are as defined above), or $C_1$–$C_5$ alkyl group, then $R^2$ represents —$CONR^9R^{10}$ wherein $R^9$ represents a hydrogen atom and $R^{10}$ represents

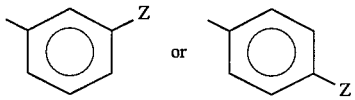

(in which Z represents a $C_1$–$C_5$ alkyl group, halogen atom, nitro group or cyano group),
or a pharmaceutically acceptable salt thereof.

2. A compound according to claim 1, wherein $R^2$ represents —$CONR^9R^{10}$ wherein $R^9$ is a hydrogen atom and $R^{10}$ represents

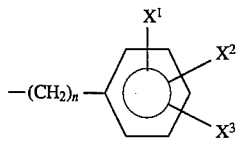

(in which $X^1$ represents a hydrogen atom, halogen atom, $C_1$–$C_5$ alkyl group, nitro group or cyano group, $X^2$ and $X^3$ each represent a hydrogen atom, and n represents 0) represents; and $R^4$, $R^5$, $R^6$, $R^7$ and $R^8$ independently each represent a hydrogen atom, hydroxy group, halogen atom, $C_1$–$C_5$ alkoxy group, nitro group, cyano group, —$SO_2R^{14}$ (in which $R^{14}$ represents a $C_1$–$C_5$ alkyl group), —$COR^{15}$ (in which $R^{15}$ represents a hydroxy group), or a $C_1$–$C_5$ alkyl group optionally substituted by a halogen atom;

with the proviso that at least one of $R^4$ to $R^5$ is a hydroxy group, and that when $R^S$ is a hydrogen atom and $R^4$ to $R^8$ independently each represent a hydrogen atom, hydroxy group, $C_1$–$C_5$ alkoxy group or $C_1$–$C_5$ alkyl group, then $R^2$ is —$CON^9R^{10}$ wherein $R^9$ represents a hydrogen atom and $R^{10}$ represents

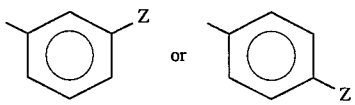

(in which Z represents a $C_1$–$C_5$ alkyl group, halogen atom, nitro group or cyano group).

3. A compound according to claim 2, wherein $R^2$ represents —$CONR^9R^{10}$ wherein $R^9$ represents a hydrogen atom and $R^{10}$ represents

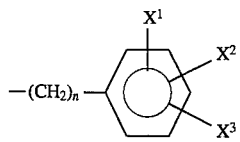

(in which $X^1$ represents a hydrogen atom, halogen atom, $C_1$–$C_5$ alkyl group, nitro group or cyano group, $X^2$ and $X^3$ each represent hydrogen atom and n represents 0);

$R^3$ represents a hydrogen atom or hydroxy group;

$R^4$ and $R^8$ independently each represent a hydrogen atom, halogen atom or nitro group;

$R^5$ and $R^7$ independently each represent a hydroxy group, halogen atom, $C_1$–$C_5$ alkoxy group, nitro group, cyano group, $SO_2R^{14}$ (in which $R^{14}$ represents a $C_1$–$C_5$ alkyl group), —$COR^{15}$ (in which $R^{15}$ represents a hydroxy group), or a $C_1$–$C_5$ alkyl group optionally substituted by a halogen atom; and $R^6$ represents a hydroxy group;

with the proviso that when $R^3$, $R^4$ and $R^8$ are each a hydrogen atom and $R^5$ and $R^7$ independently each represent a hydroxy group, $C_1$–$C_5$ alkoxy group or $C_1$–$C_5$ alkyl group, then $R^2$ is —$CONR^9R^{10}$ wherein $R^9$ represents a hydrogen atom and $R^{10}$ represents

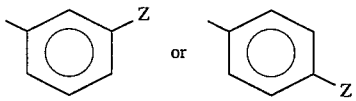

(in which Z represents a $C_1$–$C_5$ alkyl group, halogen atom, nitro group or cyano group).

4. A compound according to claim 3, in which $R^2$ represents —$CONR^9R^{10}$ wherein $R^9$ represents a hydrogen atom and $R^{10}$ represents

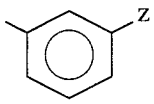

(in which Z represents a hydrogen atom or halogen atom);

$R^4$ represents a hydrogen atom;

$R^5$ represents a hydroxy group, halogen atom, $C_1$–$C_5$ alkoxy group or $C_1$–$C_5$ alkyl group; and $R^7$ represents a halogen atom, cyano group or $C_1$–$C_5$ alkyl group;

with the proviso that when $R^3$ and $R^8$ are a hydrogen atom and $R^5$ represents a hydroxy group, $C_1$–$C_5$ alkoxy group or $C_1$–$C_5$ alkyl group and $R^7$ represents a $C_1$–$C_5$ alkyl group, then Z is a halogen atom.

5. A pharmaceutical composition comprising a therapeutically effective amount of a compound according to claim 1 and a pharmaceutically acceptable carrier therefor.

6. An anticancer agent comprising a therapeutically effective amount of a compound according to claim 1 and a pharmaceutically acceptable carrier therefor.

* * * * *